(12) United States Patent
Moinet et al.

(10) Patent No.: US 8,329,738 B2
(45) Date of Patent: Dec. 11, 2012

(54) USE OF AMPK-ACTIVATING IMIDAZOLE DERIVATIVES, PREPARATION PROCESS THEREFOR AND PHARMACEUTICAL COMPOSITIONS COMPRISING THEM

(75) Inventors: Gerard Moinet, Orsay (FR);
Dominique Marais, Meulan (FR);
Sophie Hallakou-Bozec, Montrouge (FR); Christine Charon, Gometz-le-Chatel (FR)

(73) Assignee: Merck Patent Gesellschaft mit Beschränkter Haftung, Darmstadt (DE)

( * ) Notice: Subject to any disclaimer, the term of this patent is extended or adjusted under 35 U.S.C. 154(b) by 815 days.

(21) Appl. No.: 12/373,310

(22) PCT Filed: Jun. 12, 2007

(86) PCT No.: PCT/EP2007/005164
§ 371 (c)(1),
(2), (4) Date: Jan. 12, 2009

(87) PCT Pub. No.: WO2008/006432
PCT Pub. Date: Jan. 17, 2008

(65) Prior Publication Data
US 2009/0253764 A1    Oct. 8, 2009

(30) Foreign Application Priority Data

Jul. 13, 2006 (FR) ..................... 06 06415

(51) Int. Cl.
*A01N 43/50* (2006.01)
*A01N 47/28* (2006.01)
*A01N 31/14* (2006.01)
*A61K 31/415* (2006.01)
*A61K 31/17* (2006.01)
*A61K 31/08* (2006.01)

(52) U.S. Cl. ......... 514/396; 514/398; 514/588; 514/722
(58) Field of Classification Search .................. None
See application file for complete search history.

(56) References Cited

U.S. PATENT DOCUMENTS
6,482,844 B1   11/2002   He et al.

FOREIGN PATENT DOCUMENTS
DE   101 50 172 A1   4/2003
JP   57 048971      3/1982

OTHER PUBLICATIONS

Silverman, The Organic Chemistry of Drug Design and Drug Action, 2nd ed., 2004, pp. 25-34.*
Patani et al. "Bioisosterism: A Rational Approach in Drug Design", Chem.Rev., 1996, vol. 96, pp. 3147-3176.*
Kawai et al. "Structure-activity relationship study of novel NR2B-selective antagonists with arylamides to avoid reactive metabolites formation", Bioorg.Med.Chem.Lett., 2007, vol. 17, pp. 5537-5542.*
Tarumi, Y.et al "Studies on imidazole derivatives and related compounds", Journal of Heterocyclic Chemistry, (1984) pp. 529-537.
Bejamin B. Lim, "Reagents for biooganic synthesis", J. Org Chem, (1985) pp. 5111-5115, vol. 50.
Franchetti, Palmarisa et al. "Ribose-modified Mizoribine Analogs: Synthesis and Biological Evalation", Nucleosides, Nuclotides & Nucleic Acids, (2005).

* cited by examiner

*Primary Examiner* — Jeffrey S. Lundgren
*Assistant Examiner* — Stephanie Springer
(74) *Attorney, Agent, or Firm* — Millen, White, Zelano & Branigan, P.C.

(57) ABSTRACT

The invention relates to the use of imidazole derivatives of the formula (1):

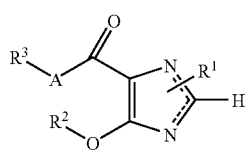

(1)

in which A, $R'_1$, $R'_2$ and $R'_3$ are as defined in the description, as AMPK activators.
The invention also relates to processes for the preparation of the said compounds, to their uses for the preparation of medicaments for the treatment of insulin resistance, diabetes and related pathologies, and also obesity, and to the pharmaceutical compositions comprising them.
Certain compounds of the formula (1) are novel and, in this respect, also form part of the invention.

15 Claims, No Drawings

USE OF AMPK-ACTIVATING IMIDAZOLE DERIVATIVES, PREPARATION PROCESS THEREFOR AND PHARMACEUTICAL COMPOSITIONS COMPRISING THEM

The present invention relates to the use of imidazole derivatives as AMP-activated protein kinase (AMPK) activators, for the prevention of or treating pathologies, such as diabetes, metabolic syndrome and obesity. The invention also relates to processes for the preparation of the said derivatives, to pharmaceutical compositions comprising them and to the use of these derivatives for the preparation of medicaments.

It has been established that AMPK is a sensor and a regulator of the homeostasis of cellular energy (Hardie D. G. and Hawley S. A., "AMP-activated protein kinase: the energy charge hypothesis revisited", Bioassays, 23, (2001), 1112; Kemp B. E. et al., "AMP-activated protein kinase, super metabolic regulator", Biochem. Soc. Transactions, 31, (2003), 162). Allosteric activation of this kinase originating from an increase in the level of AMP takes place under conditions of cellular energy depletion. This results in phosphorylation of the serine/threonine residues of the target enzymes, which leads to an adaptation of the cellular metabolism towards lower energy states. The most marked effect of the changes induced by AMPK activation is inhibition of the process of ATP consumption and activation of ATP generation, the consequence being regeneration of the stock of ATP. Examples of AMPK substrates that will be mentioned include acetyl-CoA-carboxylase (ACC) and HMG-CoA-reductase (Carling D. et al., "A common bicyclic protein kinase cascade inactivates the regulatory enzymes of fatty acid and cholesterol biosynthesis", FEBS Letters, 223, (1987), 217). Phosphorylation, and thus the inhibition ACC, leads to a reduction in fatty acid synthesis (consumption of ATP) and simultaneously to an increase in fatty acid oxidation (generation of ATP). Phosphorylation, and the inhibition of HMG-CoA reductase resulting therefrom, leads to a decrease in cholesterol synthesis. Other AMPK substrates that will also be mentioned include hormone-sensitive lipase (Garton A. J. et al., "Phosphorylation of bovine hormone-sensitive lipase by the AMP-activated protein kinase. A possible antilipolytic mechanism", Eur. J. Biochem., 179, (1989), 249), glycerol-3-phosphate acyltransferase (Muoio D. M. et al., "AMP-activated kinase reciprocally regulates triacylglycerol synthesis and fatty acid oxidation in liver and muscle: evidence that sn-glycerol-3-phosphate acyltransferase is a novel target", Biochem. J., 338, (1999), 783), malonyl-CoA-decarboxylase (Saha A. K. et al., "Activation of malonyl-CoA decarboxylase in rat skeletal muscle by contraction and the AMP-activated protein kinase activator 5-aminoimidazole-4-carboxamide-1-β-D-ribofuranoside", J. Biol. Chem., 275, (2000), 24279), and "hepatocyte nuclear factor-4-α" (Leclerc I. et al., "Hepatocyte nuclear factor-4-α involved in type-1 maturity-onset diabetes of the young is a novel target of AMP-activated protein kinase", Diabetes, 50, (2001), 1515), some of these being potential targets for the identification of compounds that are useful in metabolic syndrome.

Among the other processes assumed to be regulated by AMPK activation, but for which the AMPK substrates have not yet been identified, mention will be made of the stimulation of glucose transport in skeletal muscle and the regulation of expression of key genes in the metabolism of fatty acids and glucose in the liver (Hardie D. G. and Hawley S. A., "AMP-activated protein kinase: the energy charge hypothesis revisited", Bioassays, 23, (2001), 1112; Kemp B. E. et al., "AMP-activated protein kinase, super metabolic regulator", Biochem. Soc. Transactions, 31, (2003), 162; Musi N. and Goodyear L. J., "Targeting the AMP-activated protein kinase for the treatment of type 2 diabetes", Current Drug Targets-Immune, Endocrine and Metabolic Disorders, 2, (2002), 119). For example, a reduction in the expression of glucose-6-phosphatase (Lochhead P. A. et al., "5-aminoimidazole-4-carboxamide riboside mimics the effects of insulin on the expression of the 2 key gluconeogenic genes PEPCK and glucose-6-phosphatase", Diabetes, 49, (2000), 896), a key enzyme in the production of glucose in the liver, and of SREBP-1c (Zhou G. et al., "Role of AMP-activated protein kinase in mechanism of metformin action", J. Clin. Invest., 108, (2001), 1167), a key factor in lipogenic transcription, has been demonstrated in the course of stimulation of AMPK.

More recently, an involvement of AMPK in the regulation not only of cell metabolism, but also of the metabolism of the body as a whole, has emerged as being possible. It has been shown that the adipocyte hormone leptin induces stimulation of AMPK and, consequently, leads to an increase in fatty acid oxidation in skeletal muscle (Minokoshi Y. et al., "Leptin stimulates fatty-acid oxidation by activating AMP-activated protein kinase", Nature, 415, (2002), 339). It has also been shown that adiponectin, another adipocyte hormone that results in an improvement in carbohydrate and fat metabolism, stimulates AMPK in the liver and skeletal muscle (Yamauchi T. et al., "Adiponectin stimulates glucose utilisation and fatty acid oxidation by activating AMP-activated protein kinase", Nature Medicine, 8, (2002), 1288; Tomas E. et al., "Enhanced muscle fat oxidation and glucose transport by ACRP30 globular domain: Acetyl-CoA carboxylase inhibition and AMP-activated protein kinase activation", PNAS, 99, (2002), 16309). Under these circumstances, AMPK activation appears to be independent of the increase in the cellular levels of AMP, and is thought to be due rather to a phosphorylation by one or more kinases that have not been identified to date.

Taking into account the above-mentioned understanding of AMPK activation, beneficial effects of in vivo AMPK activation can be envisaged. In the liver, a reduction in the expression of the glucogenesis enzymes should result in a decrease in glucose production in the liver and an improvement in glucose homeostasis, whereas the inhibition and/or reduction of expression of the key enzymes of fat metabolism would lead to a reduction in fatty acid and cholesterol synthesis and to an increase in fatty acid oxidation. The stimulation of AMPK in skeletal muscle would lead to a rise in glucose uptake and in fatty acid oxidation, which would result in an improvement in glucose homeostasis and, following a reduction in intra-myocyte accumulation of triglyceride, in better action of insulin. Finally, the increase in energy expenditure should lead to a reduction in body weight. The combination of these effects in metabolic syndrome makes it possible to envisage a significant decrease in the risk of developing cardiovascular pathologies.

Many studies performed on rodents support this hypothesis (Bergeron R. et al., "Effect of 5-aminoimidazole-4-carboxamide-1β-D-ribofuranoside infusion on in vivo glucose metabolism in lean and obese Zucker rats", Diabetes, 50, (2001), 1076; Song S. M. et al., "5-Aminoimidazole-4-carboxamide ribonucleoside treatment improves glucose homeostasis in insulin-resistant diabeted (ob/ob) mice", Diabetologia, 45, (2002), 56; Halseth A. E. et al., "Acute and chronic treatment of ob/ob and db/db mice with AICAR decreases blood glucose concentrations", Biochem. Biophys. Res. Comm., 294, (2002), 798; Buhl E. S. et al., "Long-term AICAR administration reduces metabolic disturbances and lowers blood pressure in rats displaying feature of the insulin resistance syndrome", Diabetes, 51, (2002), 2199). Most of the studies are based on data obtained with AICAR, an AMPK activator (Corton J. M. et al., "5-Aminoimidazole-4-carboxamide ribonucleoside, a specific method for activating AMP-activated protein kinase in intact cells", *Eur. J. Biochem.*, 229, (1995), 558). Many in vivo studies have been performed on models of obese rodents (Bergeron R. et al., "Effect of 5-aminoimidazole-4-carboxamide-1β-D-ribofuranoside infusion on in vivo glucose metabolism in lean and obese Zucker rats", *Diabetes*, 50, (2001), 1076; Song S. M. et al., "5-Aminoimidazole-4-carboxamide ribonucleoside treatment improves glucose homeostasis in insulin-resistant diabeted (ob/ob) mice", *Diabetologia*, 45, (2002), 56; Halseth A. E. et al., "Acute and chronic treatment of ob/ob and db/db mice with AICAR decreases blood glucose concentrations", *Biochem. Biophys. Res. Comm.*, 294, (2002), 798; Buhl E. S. et al., "Long-term AICAR administration reduces metabolic disturbances and lowers blood pressure in rats displaying feature of the insulin resistance syndrome", *Diabetes*, 51, (2002), 2199). Furthermore, recent studies have shown that the antidiabetic agent metformin can activate AMPK at high concentration (Zhou G. et al., "Role of AMP-activated protein kinase in mechanism of metformin action", *J. Clin. Invest.*, 108, (2001), 1167; Musi N. et al., "Metformin increases AMP-activated protein kinase activity in skeletal muscle of subjects with type 2 diabetes", *Diabetes*, 51, (2002), 2074). Moreover, models of transgenic animals developed in recent years have shown that the action of AICAR on stimulating glucose trans-port is dependent on AMPK activation (Mu J. et al., "A role for AMP-activated protein kinase in contraction and hypoxia-regulated glucose transport in skeletal muscle", *Molecular Cell*, 7, (2001), 1085), and consequently is quite probably not produced by a non-specific ZMP effect (AICAR monophosphate). Similar studies on other tissues should make it possible to define the consequences of AMPK activation.

These factors make it possible to think that pharmacological activation of AMPK will have a beneficial effect on metabolic syndrome with an improvement in glucose and fat metabolism and a decrease in body weight.

Besides AICAR (WO 02/09726), AMPK activators have been described (WO 2004/043957; US 2005/0038068; WO 2005/028464; JP 2005-225804).

DESCRIPTION OF THE INVENTION

The present invention relates to AMPK-activating imidazole derivatives that can be used in the treatment of diabetes and related pathologies.

More particularly, the invention relates firstly to the use of the imidazole derivatives of the general formula (1) below:

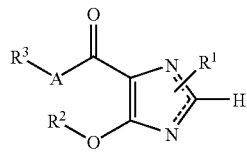

(1)

in which:
A represents —NH— or —O—;
$R^1$ is chosen from:
linear or branched ($C_1$-$C_8$)alkyl, optionally substituted by one or more groups, which may be identical or different, chosen from cycloalkyl, alkoxy, carboxyl and alkylcarbonyl;

($C_6$-$C_{14}$)aryl optionally substituted by one or more groups Y, which may be identical or different;

($C_6$-$C_{14}$)aryl($C_1$-$C_8$)alkyl, the aryl group being optionally substituted by one or more groups Y, which may be identical or different;

($C_6$-$C_{14}$)aryloxy($C_1$-$C_8$)alkyl, the aryl group being optionally substituted by one or more groups Y, which may be identical or different;

hetero($C_6$-$C_{14}$)aryl, hetero($C_6$-$C_{14}$)aryl($C_1$-$C_8$)alkyl, hetero($C_6$-$C_{14}$)aryloxy($C_1$-$C_8$)alkyl, the heteroaryl group of each of these groups itself being optionally substituted by one or more groups Y, which may be identical or different, it being understood that the said heteroaryl group may contain one or more heteroatoms chosen from nitrogen, oxygen and sulfur;

$R^2$ is chosen from:
hydrogen;
linear or branched ($C_1$-$C_8$)alkyl, optionally substituted by one or more groups, which may be identical or different, chosen from cycloalkyl, alkoxy, carboxyl and alkylcarbonyl;

($C_3$-$C_{10}$)cycloalkyl optionally substituted by one or more groups, which may be identical or different, chosen from cycloalkyl, alkoxy, carboxyl and alkylcarbonyl;

($C_6$-$C_{14}$)aryl($C_1$-$C_8$)alkyl, the aryl group being optionally substituted by one or more groups independently chosen from amino, hydroxyl, cyano, thio, halogen, ($C_1$-$C_8$)alkyl, ($C_1$-$C_8$)alkoxy, ($C_1$-$C_8$)alkylthio, ($C_1$-$C_8$)alkylamino, ($C_6$-$C_{14}$)aryl, ($C_6$-$C_{14}$)aryloxy, ($C_6$-$C_{14}$)aryl($C_1$-$C_8$)alkoxy and Y;

($C_2$-$C_{14}$)acyl, optionally substituted by one or more groups independently chosen from amino, hydroxyl, cyano, thio, halogen, ($C_1$-$C_8$)alkyl, ($C_1$-$C_8$)alkoxy, ($C_1$-$C_8$)alkylthio, ($C_1$-$C_8$)alkylamino, ($C_6$-$C_{14}$)aryl, ($C_6$-$C_{14}$)aryloxy, ($C_6$-$C_{14}$)aryl($C_1$-$C_8$)alkoxy and Y; and $R^3$ represents hydrogen or linear or branched ($C_1$-$C_8$)alkyl, optionally substituted by one or more groups, which may be identical or different, chosen from cycloalkyl, alkoxy, carboxyl and alkylcarbonyl;

Y is chosen from hydrogen, amino, nitro, hydroxyl, cyano, thio, halogen, ($C_1$-$C_8$)alkyl, ($C_1$-$C_8$)alkoxy, ($C_1$-$C_8$)alkoxycarbonyl, ($C_1$-$C_8$)alkylthio, ($C_1$-$C_8$)alkylamino, ($C_6$-$C_{14}$)aryl, ($C_6$-$C_{14}$)aryloxy and ($C_6$-$C_{14}$)aryl($C_1$-$C_8$)alkoxy,

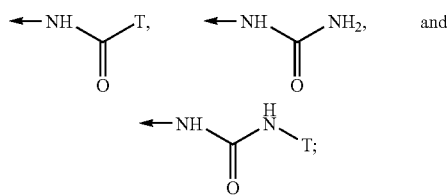

in which T is chosen from:
optionally substituted linear or branched ($C_1$-$C_8$)alkyl;
optionally substituted ($C_3$-$C_{10}$)cycloalkyl;
($C_6$-$C_{14}$)aryl optionally substituted by one or more groups independently chosen from halogen, cyano, ($C_1$-$C_8$)alkoxy, ($C_3$-$C_8$)cycloalkyl($C_1$-$C_8$)alkyl, ($C_1$-$C_8$)alkoxycarbonyl, hydroxycarbonyl and ($C_1$-$C_8$)alkylthio;

($C_6$-$C_{14}$)aryl($C_1$-$C_8$)alkyl, the aryl group being optionally substituted by one or more groups independently chosen from halogen, cyano, ($C_1$-$C_8$)alkoxy, ($C_3$-$C_{10}$)cycloalkyl($C_1$-$C_8$)alkyl, ($C_1$-$C_8$)alkoxycarbonyl, hydroxycarbonyl and ($C_1$-$C_8$)alkylthio;

hetero($C_6$-$C_{14}$)aryl, hetero($C_6$-$C_{14}$)aryl($C_1$-$C_8$)alkyl, hetero($C_6$-$C_{14}$)aryloxy($C_1$-$C_8$)alkyl, the heteroaryl group of each of these groups itself possibly being substituted by one or more groups independently chosen from halogen, ($C_1$-$C_8$)alkoxy, ($C_3$-$C_8$)cycloalkyl($C_1$-$C_8$)alkyl, ($C_1$-$C_8$)alkoxycarbonyl, hydroxycarbonyl and ($C_1$-$C_8$) alkylthio;

it being understood that the said heteroaryl group may contain one or more heteroatoms chosen from nitrogen, oxygen and sulfur.

The invention also relates to the use of the possible geometrical and/or optical isomers, epimers and tautomeric forms, possible oxidised forms, especially amine oxides, thioethers and hydrates of the compounds of the formula (1) defined above, and also to the use of the possible salts thereof with a pharmaceutically acceptable acid or base, or the pharmaceutically acceptable prodrugs of these compounds.

In the formula (1) above, the dashed line indicates the presence of a double bond between one of the two nitrogen atoms and the carbon atom bearing the hydrogen atom. The compounds of the formula (1) can thus be represented either by the formula ($1_1$) or by the formula ($1_2$):

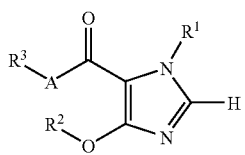

($1_1$)

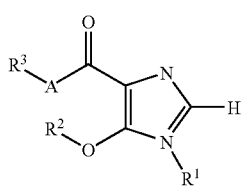

($1_2$)

Moreover, in the present description, the terms used have the following meanings:

the term "($C_1$-$C_8$)alkyl" denotes a linear or branched alkyl radical containing from 1 to 8 carbon atoms. In a non-limiting manner, among the $C_1$-$C_8$ alkyl radicals, mention may be made especially of methyl, ethyl, propyl, isopropyl, butyl, sec-butyl, tertbutyl, pentyl, hexyl and octyl radicals;

the term "($C_1$-$C_8$)acyl" denotes a group of the formula

in which R' represents hydrogen or a linear or branched hydrocarbon-based radical containing from 1 to 7 carbon atoms. In a non-limiting manner, acyl radicals containing from 1 to 8 carbon atoms that may be mentioned include formyl, acetyl, propionyl, butanoyl, pentanoyl, hexanoyl, heptanoyl, octanoyl, isopropionyl, isobutanoyl and 2,2-dimethylacetyl radicals;

the term "alkoxy" refers to the term "alkyl-oxy";
the term "halogen(s)" refers in a non-limiting manner to fluorine, chlorine or bromine;

the term "($C_6$-$C_{14}$)aryl" refers to a monocyclic or polycyclic aromatic group containing from 6 to 14 carbon atoms, at least one of the rings having a system of conjugated π electrons, and includes biaryls that may be optionally substituted, as indicated hereinabove for the aryls. Mention will be made in particular of biphenyl, phenyl, naphthyl, anthryl, phenanthryl, indanyl and tetralyl radicals;

the term "hetero($C_6$-$C_{14}$)aryl" refers to a 6- to 14-membered monocyclic or polycyclic aromatic heterocycle containing from 1 to 4 heteroatoms, the other atoms being carbon atoms. Among the heteroatoms that will be mentioned in particular are oxygen, sulfur and nitrogen. Among the heteroaryl radicals that will be mentioned more particularly are furyl, thienyl, pyridyl, pyrrolyl, pyrimidyl, pyrazinyl, oxazolyl, oxadiazolyl, isoxazolyl, quinolyl and thiazolyl radicals;

the term "($C_3$-$C_{10}$)cycloalkyl" refers to a saturated hydrocarbon-based ring and comprises monocyclic, bicyclic or polycyclic radicals containing from 3 to 10 carbon atoms. Mention will be made in a non-limiting manner of cyclopropyl, cyclobutyl, cyclopentyl and cyclohexyl radicals.

The bases that can be used for the formation of salts of compounds of the formula (1) are organic or mineral bases. The resulting salts are, for example, the salts formed with metals, and especially alkali metals, alkaline-earth metals and transition metals (such as sodium, potassium, calcium, magnesium or aluminium) or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The acids that can be used for the formation of salts of compounds of the formula (1) are mineral or organic acids. Among the mineral acids that will be mentioned, by way of example and in a non-limiting manner, are the following mineral acids: sulfuric acid, nitric acid, hydrochloric acid, hydrobromic acid, phosphoric acid, sulfamic acid. Among the organic acids that will be mentioned, by way of example and in a non-limiting manner, are the following organic acids: formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, para-toluenesulfonic acid, naphthalenemonosulfonic acid, naphthalenedisulfonic acid, laurylsulfuric acid.

The invention also relates to the chiral salts used for the separation of racemates.

By way of example, the following chiral acids are used: (+)-D-di-O-benzoyltartaric acid, (−)-L-di-O-benzoyltartaric acid, (−)-L-di-O,O'-p-toluoyl-L-tartaric acid, (+)-D-di-O,O'-p-toluoyl-L-tartaric acid, (R)-(+)-malic acid, (S)-(−)-malic acid, (+)-camphanic acid, (−)-camphanic acid, R-(−)-1,1'-binaphthalene-2,2'-diylhydrogenophosphonic acid, (+)-camphoric acid, (−)-camphoric acid, (S)-(+)-2-phenylpropionic acid, (R)-(+)-2-phenylpropionic acid, D-(−)-mandelic acid, L-(+)-mandelic acid, D-tartaric acid, L-tartaric acid, or a mixture of two or more thereof.

The chiral acid is preferentially chosen from (−)-di-O,O'-p-toluoyl-L-tartaric acid, (+)-D-di-O,O'-p-toluoyl-D-tartaric acid, (R)-(−)-1,1'-binaphthalene-2,2'-diyl hydrogen phosphate, L-tartaric acid and D-tartaric acid, or a mixture of two or more thereof.

Chiral amines may also optionally be used, for example quinine, brucine, (S)-1-(benzyloxymethyl)propylamine (III), (−)-ephedrine, (4S,5R)-(+)-1,2,2,3,4-tetramethyl-5-phenyl-1,3-oxazolidine, (R)-1-phenyl-2-p-tolylethylamine, (S)-phenylglycinol, (−)-N-methylephedrine, (+)-(2S,3R)-4-dimethylamino-3-methyl-1,2-diphenyl-2-butanol, (S)phenylglycinol or (S)-α-methylbenzylamine, or a mixture of two or more thereof.

The compounds of the formula (1) above also comprise the prodrugs of these compounds. The term "prodrugs" means compounds which, once administered into a biological system, are transformed into compounds of the formula (1) (biologically active compound), chemically and/or biologically, via spontaneous chemical reaction(s), via chemical reaction(s) catalysed with one or more enzymes and/or via metabolic chemical reaction(s).

The conventional "prodrugs" are formed using groups linked to a functional group, such as hydroxyl, thio, carboxyl, alkylcarbonyl, amino, alkylamino or dialkylamino, associated with the AMPK activator, and which become separated in vivo.

Non-limiting examples of conventional "prodrugs" that may be mentioned include carboxylic esters, in which the ester group is alkyl, aryl, aralkyl, acyloxyalkyl or alkoxycarbonyloxyalkyl, and also the esters of hydroxyl, thio and amine groups, in which the attached group is an acyl, an alkoxycarbonyl, an aminocarbonyl, a phosphate or a sulfate. The prodrugs should undergo at least one chemical transformation to produce the compound that is biologically active, or alternatively should be a precursor of the biologically active compound. In certain cases, the prodrugs is biologically active, but generally, however, less than the compound itself, and is useful for improving the efficacy or the non-toxicity by means of improving the oral bioavailability, the pharmacodynamic half-life and the like.

Among the compounds of the formula (1), which are subjects of the use according to the present invention, some are already known.

Thus, U.S. Pat. No. 4,140,788 describes imidazole derivatives used in the treatment of "Sarcoma 180" tumour and corresponding to the general formula (1) in which A represents —NH—, and $R^1$ and $R^3$ represent, independently of each other, hydrogen, $(C_1-C_3)$alkyl, $(C_3-C_5)$alkenyl, or benzyl optionally substituted by $(C_1-C_3)$alkoxy.

Patent JP-57048971 discloses imidazole derivatives with anti-inflammatory activity of the general formula (1), in which A=—NH—, $R^3$ and $R^2$ each represent a hydrogen atom, and $R^1$ represents benzyl or benzyl substituted in position 4 with nitro or methoxy. These same compounds also appear in the publication by Tarumi Y. et al., *J. Het. Chem.*, 21(3), (1984), 849-854.

The 4-carbomethoxy-5-hydroxyimidazole derivatives described by Hosmane R. S. and B. B. Lim (*Tet. Lett.*, 26(16), (1985), 1915-1918; *J. Org. Chem.*, 50(25), (1985), 5111-5115) correspond to the general formula (1) in which A represents oxygen, $R^3$ represents methyl, $R^2$ represents hydrogen and $R^1$ is chosen from hydrogen, $(C_1-C_4)$alkyl, benzyl and cyclohexyl.

Also, 5-methoxy-1-methyl-1H-imidazole-4-carboxamide is known (*J. Het. Chem.*, 20(4), (1983), 875-885).

The present invention also relates to the novel imidazole derivatives of the general formula (1'):

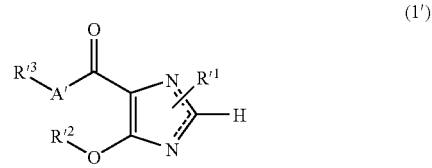

in which:

A represents —NH— or —O—;

$R'^1$ is chosen from:

linear or branched $(C_5-C_8)$alkyl, optionally substituted by one or more groups, which may be identical or different, chosen from cycloalkyl, alkoxy, carboxyl and alkylcarbonyl;

$(C_6-C_{14})$aryl optionally substituted by one or more groups Y', which may be identical or different;

$(C_6-C_{14})$aryl$(C_1-C_8)$alkyl, the aryl group being optionally substituted by one or more groups Y, which may be identical or different;

$(C_6-C_{14})$aryloxy$(C_1-C_8)$alkyl, the aryl group being optionally substituted by one or more groups Y', which may be identical or different;

hetero$(C_6-C_{14})$aryl, hetero$(C_6-C_{14})$aryl$(C_1-C_8)$alkyl, hetero$(C_6-C_{14})$aryloxy$(C_1-C_8)$alkyl, the heteroaryl group of each of these groups itself being optionally substituted by one or more groups Y', which may be identical or different, it being understood that the said heteroaryl group may contain one or more heteroatoms chosen from nitrogen, oxygen and sulfur;

$R'^2$ is chosen from:

hydrogen;

linear or branched $(C_1-C_8)$alkyl, optionally substituted by one or more groups, which may be identical or different, chosen from cycloalkyl, alkoxy, carboxyl and alkylcarbonyl;

$(C_3-C_{10})$cycloalkyl optionally substituted by one or more groups, which may be identical or different, chosen from cycloalkyl, alkoxy, carboxyl and alkylcarbonyl;

$(C_6-C_{14})$aryl$(C_1-C_8)$alkyl, the aryl group being optionally substituted by one or more groups independently chosen from amino, hydroxyl, cyano, thio, halogen, $(C_1-C_8)$alkyl, $(C_1-C_8)$alkoxy, $(C_1-C_8)$alkylthio, $(C_1-C_8)$alkylamino, $(C_6-C_{14})$aryl, $(C_6-C_{14})$aryloxy, $(C_6-C_{14})$aryl$(C_1-C_8)$alkoxy and Y';

$(C_2-C_{14})$acyl, optionally substituted by one or more groups independently chosen from amino, hydroxyl, cyano, thio, halogen, $(C_1-C_8)$alkyl, $(C_1-C_8)$alkoxy, $(C_1-C_8)$alkylthio, $(C_1-C_8)$alkylamino, $(C_6-C_{14})$aryl, $(C_6-C_{14})$aryloxy, $(C_6-C_{14})$aryl$(C_1-C_8)$alkoxy and Y'; and $R^3$ represents hydrogen or linear or branched $(C_1-C_8)$alkyl, optionally substituted by one or more groups, which may be identical or different, chosen from cycloalkyl, alkoxy, carboxyl and alkylcarbonyl;

Y is chosen from hydrogen, amino, nitro, hydroxyl, cyano, thio, halogen, $(C_1-C_8)$alkyl, $(C_1-C_8)$alkoxy, $(C_1-C_8)$alkoxycarbonyl, $(C_1-C_8)$alkylthio, $(C_1-C_8)$alkylamino, $(C_6-C_{14})$aryl, $(C_6-C_{14})$aryloxy and $(C_6-C_{14})$aryl$(C_1-C_8)$alkoxy,

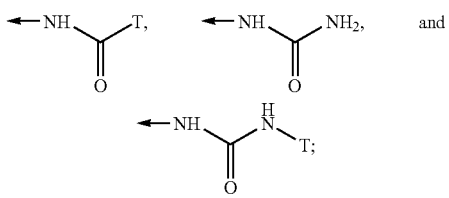
and
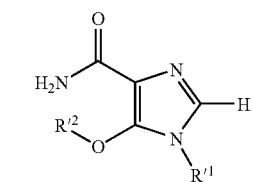

in which T is chosen from:

optionally substituted linear or branched $(C_1-C_8)$alkyl;

optionally substituted $(C_3-C_{10})$cycloalkyl;

$(C_6-C_{14})$aryl optionally substituted by one or more groups independently chosen from halogen, cyano, $(C_1-C_8)$ alkoxy, $(C_3-C_8)$cycloalkyl$(C_1-C_8)$alkyl, $(C_1-C_8)$alkoxycarbonyl, hydroxycarbonyl and $(C_1-C_8)$alkylthio;

$(C_6-C_{14})$aryl$(C_1-C_8)$alkyl, the aryl group being optionally substituted by one or more groups independently chosen from halogen, cyano, $(C_1-C_8)$alkoxy, $(C_3-C_{10})$cycloalkyl$(C_1-C_8)$alkyl, $(C_1-C_8)$alkoxycarbonyl, hydroxycarbonyl and $(C_1-C_8)$alkylthio;

hetero$(C_6-C_{14})$aryl, hetero$(C_6-C_{14})$aryl$(C_1-C_8)$alkyl, hetero$(C_6-C_{14})$aryloxy$(C_1-C_8)$alkyl, the heteroaryl group of each of these groups itself possibly being substituted by one or more groups independently chosen from halogen, $(C_1-C_8)$alkoxy, $(C_3-C_8)$cycloalkyl$(C_1-C_8)$alkyl, $(C_1-C_8)$alkoxycarbonyl, hydroxycarbonyl and $(C_1-C_8)$ alkylthio;

it being understood that the said heteroaryl group may contain one or more heteroatoms chosen from nitrogen, oxygen and sulfur;

with the restriction that if $R'^2$ represents hydrogen, then $R'^1$ cannot represent benzyl or benzyl substituted in position 4 with nitro or methoxy, and the possible geometrical and/or optical isomers, epimers and tautomeric forms, possible oxidised forms, especially amine oxide, thioethers and hydrates thereof, and also the possible addition salts thereof with a pharmaceutically acceptable acid or base, or alternatively the pharmaceutically acceptable prodrugs of these compounds.

It should be understood that all the compounds of the general formula (1') are included in the general formula (1) defined previously. Thus, unless otherwise indicated, all the definitions given for the compounds of the formula (1) apply to the compounds of the formula (1').

In the remainder of the present description, and unless otherwise indicated, the term "compound(s) of the formula (1)" means "compound(s) of the formula (1) or of the formula (1')".

For the purposes of the present invention, the compounds of the formula (1) for which A represents —NH—, and more preferably the compounds of the formula (1) for which A represents —NH— and $R^3$ represents hydrogen, are preferred.

According to one variant, the compounds of the formula (1) for which A represents —O— are preferred.

A first preferred subgroup according to the invention corresponds to the compounds of the formula (1') in which A represents —NH— and $R'^3$ represents hydrogen, the said subgroup being represented by formula (1A):

(1A)

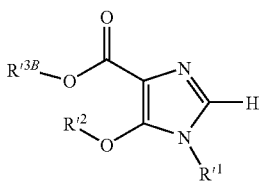

in which $R'^1$ and $R'^2$ are as defined above for the compounds of the formula (1'), with the restriction that if $R'^2$ represents hydrogen, then $R'^1$ cannot represent benzyl or benzyl substituted in position 4 with nitro or methoxy, the possible geometrical and/or optical isomers, epimers and tautomeric forms thereof, possible oxidised forms, especially amine oxide or thioethers, and the solvates and hydrates of these compounds;

and also the possible salts thereof with a pharmaceutically acceptable acid or base, or alternatively the pharmaceutically acceptable prodrugs of these compounds.

A second preferred subgroup corresponds to the compounds of the formula (1') according to the invention, in which -A- is —O—, and represented by formula (1B):

(1B)

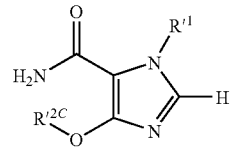

in which $R'^1$ and $R'^2$ are as defined above, and $R'^{3B}$ represents $(C_1-C_8)$alkyl, with the restriction that if $R'^2$ represents hydrogen, then $R'^1$ cannot represent benzyl or benzyl substituted in position 4 with nitro or methoxy, the possible geometrical and/or optical isomers, epimers and tautomeric forms thereof, possible oxidised forms, especially amine oxide or thioethers, and the solvates and hydrates of these compounds;

and also the possible salts thereof with a pharmaceutically acceptable acid or base, or alternatively the pharmaceutically acceptable prodrugs of these compounds.

A third preferred subgroup corresponds to the compounds of the formula (1'), according to the invention, represented by formula (1C):

(1C)

in which $R'^1$ is as defined above and $R'^{2C}$ is chosen from hydrogen, $(C_1-C_8)$alkyl and $(C_2-C_{14})$acyl, with the restriction that if $R'^2$ represents hydrogen, then $R'^1$ cannot represent benzyl or benzyl substituted in position 4 with nitro or methoxy, the possible geometrical and/or optical isomers, epimers and tautomeric forms thereof, possible oxidised forms, especially amine oxide or thioethers, and the solvates and hydrates of these compounds;

and also the possible salts thereof with a pharmaceutically acceptable acid or base, or alternatively the pharmaceutically acceptable prodrugs of these compounds.

Among the compounds of the formula (1C) defined above, also preferred are the compounds of the formula (1Ca):

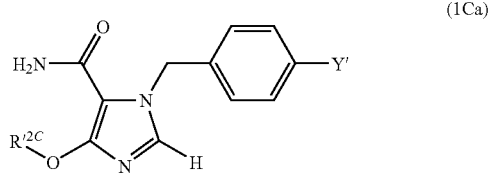

(1Ca)

in which $R'^{2C}$ represents hydrogen, $(C_1-C_8)$alkyl or $(C_2-C_{14})$acyl and Y' is as defined above for the compounds of the formula (1'), with the restriction that if $R'^2$ represents hydrogen, then Y' cannot represent hydrogen, nitro or methoxy, the possible geometrical and/or optical isomers, epimers and tautomeric forms thereof, possible oxidised forms, especially amine oxide or thioethers, and the solvates and hydrates of these compounds, and also the possible salts thereof with a pharmaceutically acceptable acid or base, or alternatively the pharmaceutically acceptable prodrugs of these compounds.

A more particularly preferred subgroup among the compounds of the formula (1Ca) is defined by the compounds represented by formula (1Caa):

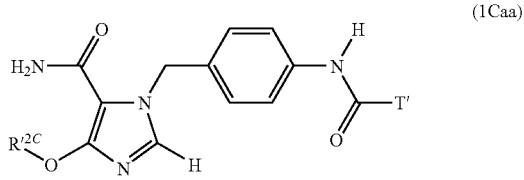

(1Caa)

in which $R'^{2C}$ represents hydrogen, $(C_1-C_8)$alkyl or $(C_2-C_{14})$acyl and T' is as defined above for the compounds of the formula (1'), the possible geometrical and/or optical isomers, epimers and tautomeric forms thereof, possible oxidised forms, especially amine oxide or thioethers, and the solvates and hydrates of these compounds;

and also the possible salts thereof with a pharmaceutically acceptable acid or base, or alternatively the pharmaceutically acceptable prodrugs of these compounds.

Another more particularly preferred group among the compounds of the formula (1Ca) defined above consists of the compounds represented by formula (1Cb):

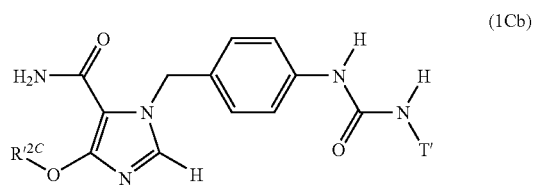

(1Cb)

in which $R'^{2C}$ represents hydrogen, $(C_1-C_8)$alkyl or $(C_2-C_{14})$acyl and T' is as defined above for the compounds of the formula (1'), the possible geometrical and/or optical isomers, epimers and tautomeric forms thereof, possible oxidised forms, especially amine oxide or thioethers, and the solvates and hydrates of these compounds;

and also the possible salts thereof with a pharmaceutically acceptable acid or base, or alternatively the pharmaceutically acceptable prodrugs of these compounds.

More particularly, the preferred compounds of the formula (1) are chosen from:

01) ethyl 5-hydroxy-1-(2-phenoxyethyl)-1H-imidazole-4-carboxylate;
02) ethyl 5-hydroxy-1-[2-(-4-cyanophenoxy)ethyl]-1H-imidazole-4-carboxylate;
03) ethyl 5-hydroxy-1-[2-(-4-fluorophenoxy)ethyl]-1H-imidazole-4-carboxylate;
04) 5-hydroxy-1-{2-[-4(methoxycarbonyl)phenoxy]ethyl}-1H-imidazole-4-carboxylate;
05) ethyl 1-benzyl-5-methoxy-1H-imidazole-4-carboxylate;
06) 1-[2-(4-fluorophenoxy)ethyl]-5-hydroxy-1H-imidazole-4-carboxamide;
07) 5-hydroxy-1-(2-phenoxyethyl)-1H-imidazole-4-carboxamide;
08) 1-[2-(4-cyanophenoxy)ethyl]-5-hydroxy-1H-imidazole-4-carboxamide;
09) methyl 4-[2-(4-carbamoyl-5-hydroxyimidazol-1-yl)ethoxy]benzoate;
10) 5-hydroxy-3-[4-(3-methoxybenzoylamino)benzyl]-3H-imidazole-4-carboxamide;
11) 3-(4-acetylaminobenzyl)-5-hydroxy-3H-imidazole-4-carboxamide;
12) 3-(4-benzoylaminobenzyl)-5-hydroxy-3H-imidazole-4-carboxamide;
13) 3-[4-(cyclohexanecarbonylamino)benzyl]-5-hydroxy-3H-imidazole-4-carboxamide;
14) 5-hydroxy-3-[4-(4-methoxybenzoylamino)benzyl]-3H-imidazole-4-carboxamide;
15) 3-[4-(3,3-dimethylbutyrylamino)benzyl]-5-hydroxy-3H-imidazole-4-carboxamide;
16) 5-hydroxy-3-[4-(4-fluorobenzoylamino)benzyl]-3H-imidazole-4-carboxamide;
17) 5-hydroxy-3-{4-[(naphthalene-1-carbonyl)amino]benzyl}-3H-imidazole-4-carboxamide;
18) 3-[4-(3-cyclopentylpropionylamino)benzyl]-5-hydroxy-3H-imidazole-4-carboxamide;
19) 5-hydroxy-3-(4-fluorobenzyl)imidazole-4-carboxamide;
20) 5-hydroxy-3-(4-chlorobenzyl)imidazole-4-carboxamide;
21) 5-hydroxy-3-[4-(ethoxycarbonyl)benzyl]imidazole-4-carboxamide;
22) 5-hydroxy-3-phenylimidazole-4-carboxamide;
23) 5-hydroxy-3-(2-phenoxyethyl)-3H-imidazole-4-carboxamide;
24) 3-[2-(4-fluorophenoxy)ethyl]-5-hydroxy-3H-imidazole-4-carboxamide;

25) 3-[2-(4-cyanophenoxy)ethyl]-5-hydroxy-3H-imidazole-4-carboxamide;
26) methyl 4-[2-(5-carbamoyl-4-hydroxyimidazol-1-yl)ethoxy]benzoate;
27) 3-(4-aminobenzyl)-5-hydroxy-3H-imidazole-4-carboxamide;
28) 4-carboxamide-5-hydroxy-3-phenylimidazole;
29) 5-methoxy-3-(4-nitrobenzyl)-3H-imidazole-4-carboxamide;
30) 5-benzyloxy-3-(4-nitrobenzyl)-3H-imidazole-4-carboxamide;
31) 5-hydroxy-3-[4-(3-methoxybenzoylamino)benzyl]-3H-imidazole-4-carboxamide;
32) 3-{4-[2-(4-chlorophenyl)acetylamino]benzyl}-5-hydroxy-3H-imidazole-4-carboxamide;
33) 5-hydroxy-3-[4-(4-chlorobenzoylamino)benzyl]-3H-imidazole-4-carboxamide;
34) 3-(4-hexanoylaminobenzyl)-5-hydroxy-3H-imidazole-4-carboxamide;
35) 5-hydroxy-3-[4-(2-fluorobenzoylamino)benzyl]-3H-imidazole-4-carboxamide;
36) 5-hydroxy-3-[4-(4-methylbenzoylamino)benzyl]-3H-imidazole-4-carboxamide;
37) 5-hydroxy-3-[4-(2-methoxybenzoylamino)benzyl]-3H-imidazole-4-carboxamide;
38) 5-hydroxy-3-{4-[(naphthalene-2-carbonyl)amino]benzyl}-3H-imidazole-4-carboxamide;
39) 5-hydroxy-3-{4-[2-(4-nitrophenyl)acetylamino]benzyl}-3H-imidazole-4-carboxamide;
40) 5-hydroxy-3-[4-(2-phenylbutyrylamino)benzyl]-3H-imidazole-4-carboxamide;
41) 3-[4-(2-furan-2-ylacetylamino)benzyl]-5-hydroxy-3H-imidazole-4-carboxamide;
42) 5-hydroxy-3-[4-(2-thiophen-2-ylacetylamino)benzyl]-3H-imidazole-4-carboxamide;
43) 5-methoxy-3-{4-[(naphthalene-1-carbonyl)amino]benzyl}-3H-imidazole-4-carboxamide;
44) 5-acetyloxy-3-[4-(4-acetylamino)benzyl]-3H-imidazole-4-carboxamide;
45) 5-hydroxy-3-[4-(3-phenylureido)benzyl]-3H-imidazole-4-carboxamide;
46) 5-hydroxy-3-{4-[3-(4-methoxyphenyl)ureido]benzyl}-3H-imidazole-4-carboxamide;
47) 5-hydroxy-3-{4-[3-(4-chlorophenyl)ureido]benzyl}-3H-imidazole-4-carboxamide;
48) 3-[4-(3-cyclohexylureido)benzyl]-5-hydroxy-3H-imidazole-4-carboxamide;
49) 3-[4-(3-cyclopentylureido)benzyl]-5-hydroxy-3H-imidazole-4-carboxamide;
50) 5-hydroxy-3-[4-(3-naphthalen-1-ylureido)benzyl]-3H-imidazole-4-carboxamide;
51) 5-hydroxy-3-[4-(3-naphthalen-2-ylureido)benzyl]-3H-imidazole-4-carboxamide;
52) 5-hydroxy-3-{4-[3-(5,6,7,8-tetrahydronaphthalen-1-yl)ureido]benzyl}-3H-imidazole-4-carboxamide;
53) 3-[4-(3-ethylureido)benzyl]-5-hydroxy-3H-imidazole-4-carboxamide;
54) 3-[4-(3-benzylureido)benzyl]-5-hydroxy-3H-imidazole-4-carboxamide;
55) 5-hydroxy-3-[4-(3-m-tolylureido)benzyl]-3H-imidazole-4-carboxamide;
56) 5-hydroxy-3-{4-[3-(3-methoxyphenyl)ureido]benzyl}-3H-imidazole-4-carboxamide;
57) 3-{4-[3-(2-fluorobenzyl)ureido]benzyl}-5-hydroxy-3H-imidazole-4-carboxamide;
58) 5-hydroxy-3-{4-[3-(2-methoxyphenyl)ureido]benzyl}-3H-imidazole-4-carboxamide;
59) 5-hydroxy-3-{4-[3-(4-ethylphenyl)ureido]benzyl}-3H-imidazole-4-carboxamide;
60) 5-hydroxy-3-{4-[3-(3-methylsulfanylphenyl)ureido]benzyl}-3H-imidazole-4-carboxamide;
61) 5-hydroxy-3-{4-[3-(4-methylsulfanylphenyl)ureido]benzyl}-3H-imidazole-4-carboxamide;
62) 5-hydroxy-3-[4-(3-indan-5-ylureido)benzyl]-3H-imidazole-4-carboxamide;
63) 5-hydroxy-3-{4-[3-(4-fluorophenyl)ureido]benzyl}-3H-imidazole-4-carboxamide;
64) 5-hydroxy-3-{4-[3-(2-chlorophenyl)ureido]benzyl}-3H-imidazole-4-carboxamide;
65) 5-hydroxy-3-{4-[3-(2-trifluoromethylphenyl)ureido]benzyl}-3H-imidazole-4-carboxamide;
66) 5-hydroxy-3-{4-[3-(3-trifluoromethylphenyl)ureido]benzyl}-3H-imidazole-4-carboxamide;
67) 5-hydroxy-3-{4-[3-(4-trifluoromethylphenyl)ureido]benzyl}-3H-imidazole-4-carboxamide;
68) ethyl 3-{3-[4-(5-carbamoyl-4-hydroxyimidazol-1-ylmethyl)phenyl]ureido}benzoate;
69) 3-{3-[4-(5-carbamoyl-4-hydroxyimidazol-1-ylmethyl)phenyl]ureido}benzoic acid;
70) ethyl 4-{3-[4-(5-carbamoyl-4-hydroxyimidazol-1-ylmethyl)phenyl]ureido}benzoate;
71) 4-{3-[4-(5-carbamoyl-4-hydroxyimidazol-1-ylmethyl)phenyl]ureido}benzoic acid;
72) ethyl 2-{3-[4-(5-carbamoyl-4-hydroxyimidazol-1-ylmethyl)phenyl]ureido}benzoate; and
73) ethyl {3-[4-(5-carbamoyl-4-hydroxyimidazol-1-ylmethyl)phenyl]ureido}acetate.

The present invention also relates to a process for the preparation of these compounds of the formula (1) or (1'), characterised in that a compound of the formula (4a) or (4b):

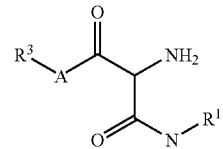

(4a)

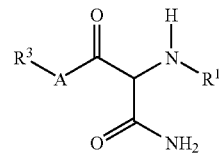

(4b)

in which $R^1$ and $R^3$ are as defined above, is used in a cyclisation reaction, the said cyclisation reaction being performed according to known methods, for example with ethyl orthoformate [$HC(OC_2H_5)_3$], to give the imidazoles of the formula ($1_{OH}$):

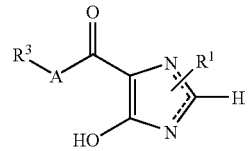

($1_{OH}$)

corresponding to the compounds of the formula (1), in which R² represents hydrogen, in which imidazoles of the formula $(1_{OH})$ the hydroxyl group may be etherified, according to standard techniques known to those skilled in the art, for example using a reagent of the formula R—X, in which R has the same definition as R² defined above, with the exception of hydrogen, and X represents a halogen atom, to give the compounds of the formula $(1_R)$:

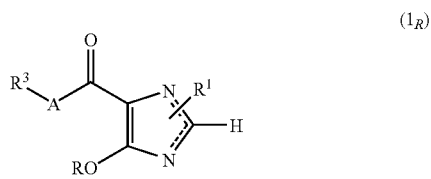

the set of compounds of the formulae $(1_{OH})$ and $(1_R)$ forming the set of compounds of the formula (1).

The starting reagent (4) is either commercially available or obtained via standard chemical synthetic routes known to those skilled in the art.

The general process for the preparation of the compounds of the formula (1) described above applies mutatis mutandis to the compounds of the formula (1').

According to one advantageous embodiment, the compounds of the formula (1A)—i.e. the compounds of the formula (1') for which R'$_3$=H and A=NH—can also be prepared according to the following reaction scheme:

phosphate (DEPC), carbonyldiimidazole, diphenylphosphorylazide (DPPA), or more particularly the dicyclohexylcarbodiimide/1-hydroxybenzotriazole (HBTO) couple, or the diethyl azodicarboxylate/triphenylphosphine couple or the dicyclohexylcarbodiimide/1-hydroxybenzotriazole couple. The dicyclohexylcarbodiimide/1-hydroxybenzotriazole couple is more particularly preferred. The reaction is preferably performed in the presence of an inert solvent, such as aromatic hydrocarbons, for example benzene, toluene or xylene; a halogenated hydrocarbon and in particular aliphatic halogenated hydrocarbons, for instance methylene chloride, dichloroethane or chloroform; esters, for instance ethyl acetate or propyl acetate, ethers, such as diethyl ether, tetrahydrofuran and dioxane; amides, such as dimethylformamide, dimethylacetamide or hexamethylphosphorotriamide; and nitriles, such as acetonitrile. Ethers, such as tetrahydrofuran, halogenated hydrocarbons, such as methylene chloride, amides, such as dimethylformamide and esters, such as ethyl acetate are more particularly preferred. The reaction can take place over a wide temperature range, in particular between −10° C. and 50° C. and preferably between −10° C. and room temperature. The reaction time varies according to many factors and in particular the reaction temperature and the reagents used. It is preferably between 30 minutes and 24 hours;

the compound of the formula (3A) is obtained via the action of ammonia on compound (2A), in a solvent, such as an alcohol, for example methanol or ethanol, at a temperature of between 0° C. and 30° C. and preferably between 10° C. and room temperature. The reaction time varies according to

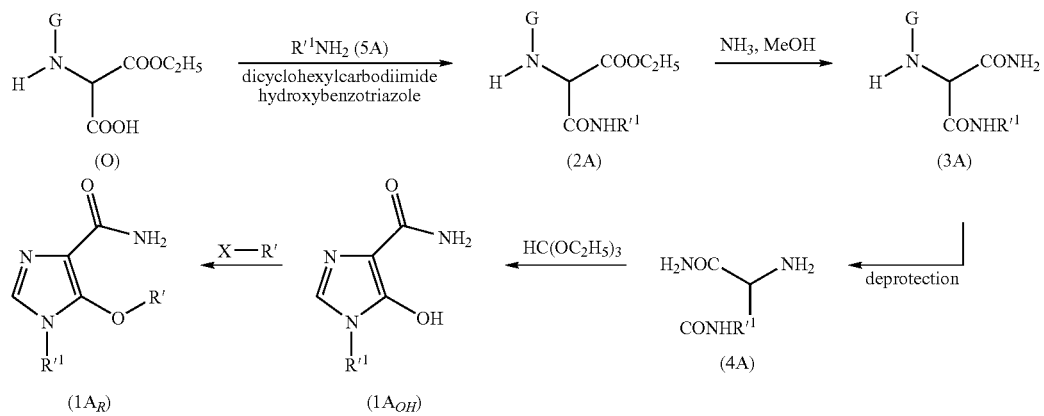

in which scheme:

G represents a protecting group chosen from Z (benzyloxycarbonyl), BOC (tertbutoxycarbonyl) and Fmoc (fluorenemethoxycarbonyl).

The starting malonate (O) was prepared according to the method described in *J. Org. Chem.*, 54(6), (1989), 1364-70. The compounds of the formulae $(1A_R)$ and $(1A_{OH})$ form the set of compounds of the formula (1A) defined above and are obtained in four steps from the malonate (O):

compound (2A) is obtained by reacting compound (5A), in which R'¹ has the definition given above, with the malonate monoester (O) in the presence or absence of a base; it is preferably performed in an inert solvent in the presence of a coupling agent. There is no particular restriction as to the choice of coupling agents. The preferred agents are, for example, dicyclohexylcarbodiimide (DCC), diethyl cyano-many factors and in particular the reaction temperature and the reagents used. It is preferably between 30 minutes and 24 hours;

the compound of the formula (4A) is obtained by deprotection ("cleavage") of the protecting group G, for example via hydrogenolysis according to known techniques, for example as described in Greene et al., "Protective Groups in Organic Synthesis", 2$^{nd}$ ed., John Wiley & Sons, New York, 1999, 17-292;

the cyclisation of (4A) to $(1A_{OH})$ is performed according to Tarumi et al. (U.S. Pat. No. 4,140,788), i.e. by treating (4A) with an excess of ethyl orthoformate in a polar solvent, such as an alcohol, for example methanol or ethanol, at a temperature of between 20° C. and the reflux temperature of the medium, in the presence of catalytic amounts of acids, such as para-toluenesulfonic acid, hydrochloric acid, acetic acid or sulfuric acid, and for a time of between 2 hours and 24 hours and preferably between 2 hours and 8 hours;

the treatment of (1A$_{OH}$) with R'—X according to Atsumi et al. (U.S. Pat. No. 4,140,788) allows the production of compound (1A$_R$), in which R' has the same definition as R'$^2$, with the exception of hydrogen, and X represents a halogen, the set of compounds of the formulae (1A$_{OH}$) and (1A$_R$) forming the set of compounds of the formula (1A).

According to another advantageous embodiment, the compounds of the formula (1B)—i.e. the compounds of the formula (1') for which R'$_3$=R'$^{3B}$ and A=O—can also be prepared according to the following reaction scheme:

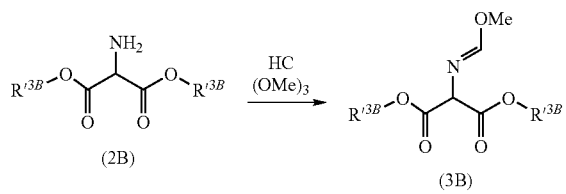

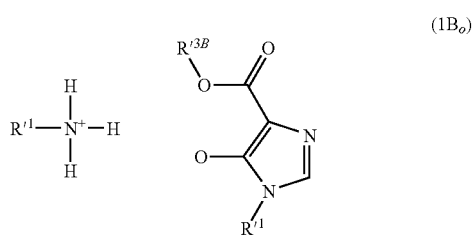

By treating an aqueous solution of (1B$_O$) with an acid, and more particularly hydrochloric acid, (1B$_{OH}$) is obtained, and is then converted into (1B$_R$) according to Atsumi et al. (U.S. Pat. No. 4,140,788), in which R' has the same definition as R'$^2$, with the exception of hydrogen, the set of compounds of the formulae (1B$_{OH}$) and (1B$_R$) forming the set of compounds of the formula (1B).

According to another advantageous embodiment, the compounds of the formula (1C)—i.e. the compounds of the formula (1') for which R'$^3$=H and A=NH—can also be prepared according to the following reaction scheme:

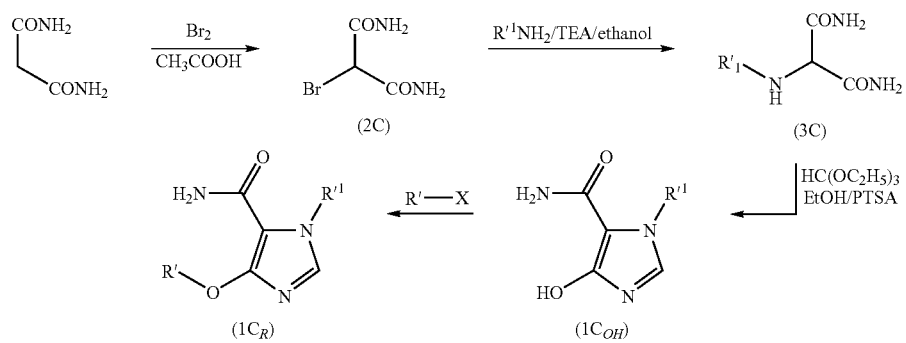

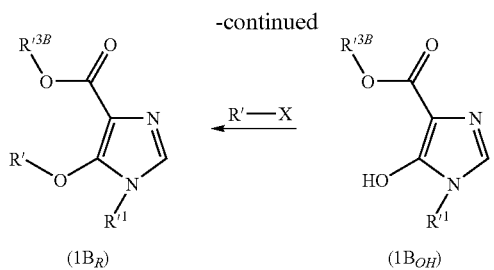

in which scheme:

the amino malonate (2B) is either obtained from commercial sources or prepared according to the literature (for example according to EP 811 602). Compound (3B) is obtained from (2B) according to Lim et al. (*J. Org. Chem.*, 50(25), (1985), 5111-5115). The cyclisation reaction of (3B) with (5) to give (1B$_{OH}$) is also performed according to Lim et al. (ibid.) (the acetonitrile or methanol can advantageously be replaced with ethyl acetate), and the reaction time is preferably between 2 hours and 24 hours. Compound (1B$_{OH}$) is generally obtained in the form of the ammonium salt (1B$_O$) with the amine (5):

The bromomalonamide (2C) is obtained, for example, according to Hata Tsujiaki (*Bull. Chem. Soc. Jap.*, 37(24), (1964), 547-549). The production of (3C) by coupling R'$^1$NH$_2$ with (2C), the production of (1C$_{OH}$) by cyclising (3C) via coupling with ethyl orthoformate, and the reaction with R'—X, in which R' is as defined above, to obtain (1C$_R$) are performed according to Atsumi et al. (U.S. Pat. No. 4,464, 531). The coupling of R'$^1$NH$_2$ with (3C) is preferably performed in an anhydrous alcoholic solvent (for example methanol or ethanol), in the presence of a base, such as triethylamine or pyridine, for a time preferably of between 2 hours and 8 hours, and at a temperature of between room temperature and the reflux temperature of the solvent. The cyclisation of (3C) is performed with an excess of ethyl orthoformate, for example between 4 and 10 equivalents relative to (3C), in an anhydrous alcoholic solvent, such as those defined above, for a time preferably of between 2 hours and 8 hours and at a temperature of between room temperature and the reflux temperature of the solvent.

The set of compounds of the formulae (1C$_{OH}$) and (1C$_R$) forms the set of compounds of the formula (1C).

According to yet another advantageous embodiment, the compounds of the formulae (1Caa) and (1Cb) defined above can also be prepared according to the following reaction scheme:

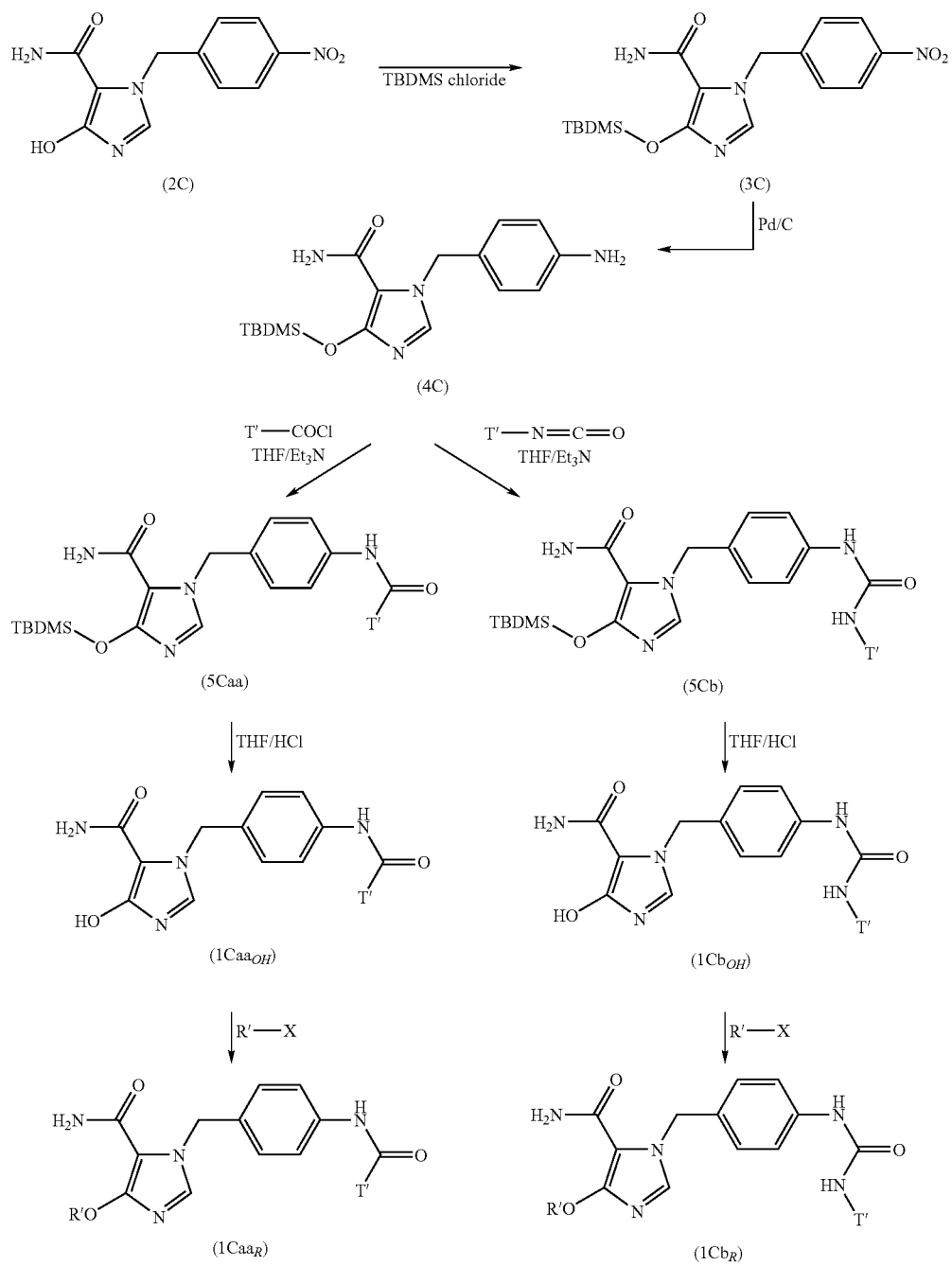

Compound (2C) is obtained according to Tarumi et al. (*J Het. Chem.*, 21(3), (1984), 849). The reaction of (2C) with tert-butyldimethylsilyl chloride (TBDMS) is performed according to the methods described in the literature (for example Greene et al., "Protective Groups in Organic Synthesis", 2$^{nd}$ ed., John Wiley & Sons, New York, 1999, 17-292; Slebocka-Tilk et al., *J. Org. Chem.*, 50, (1985), 4638). Preferably, compound (2C) is reacted with TBDMS in a solvent, such as dimethylformamide, toluene or acetone, in the presence of imidazole (1 eq.), at a temperature of between 20° C. and 80° C., for a time of between 2 hours and 8 hours. Via catalytic reduction of (3C) according to known literature methods, (4C) is obtained.

Production of the Amides of the Formula (1Ca)

Compound (4C) is placed in a solvent, such as anhydrous tetrahydrofuran, dimethylformamide, toluene or the like. It is then treated, according to the known techniques of organic chemistry, with an acyl chloride, at a temperature preferably of between 20° C. and the reflux temperature of the solvent, and for a time preferably of between 2 hours and 72 hours. Compound (5Ca) is thus obtained, and is not isolated. Cleavage of the silyl ether is then performed by treating compound (5Ca) in acidic medium according to the known techniques of organic chemistry, to give compound (5Ca$_{OH}$), which is then optionally treated with a compound of the formula R'—X, as indicated previously, to give compound (5Ca$_R$).

The set of compounds of the formulae ($5Ca_{OH}$) and ($5Ca_R$) forms the set of compounds of the formula ($5Ca$).

Production of the Ureas of the Formula (1Cb)

These ureas are obtained via a process similar to that described for the preparation of compounds (5Ca), but replacing the acyl chloride with an isocyanate.

The present invention also relates to the use of the compounds of the formula (1) or of pharmaceutically acceptable salts thereof, for the production of pharmaceutical preparations.

The present invention also relates to pharmaceutical preparations comprising at least one compound of the formula (1) and/or a pharmaceutically acceptable salt thereof.

The present invention also relates to pharmaceutical compositions comprising a pharmaceutically effective amount of at least one compound of the formula (1) and/or a salt thereof, in combination with one or more pharmaceutically acceptable vehicles.

The pharmaceutical compositions of the invention comprise formulations, such as granules, powders, tablets, gel capsules, syrups, emulsions and suspensions, and also the forms used for non-oral administration, for example injections, sprays, suppositories and the like.

The pharmaceutical forms can be prepared via known conventional techniques.

The preparation of a solid pharmaceutical form for oral administration can be performed, for example, according to the following process: an excipient (for example lactose, sucrose, starch, mannitol and the like), a disintegrant (for example calcium carbonate, calcium carboxymethylcellulose, alginic acid, sodium carboxymethylcellulose, colloidal silicon dioxide, sodium croscarmellose, crospovidone, guar gum, magnesium aluminium silicate, microcrystalline cellulose, cellulose powder, pregelatinised starch, sodium alginate, starch glycolate and the like), a binder (for example α-starch, gum arabic, carboxymethylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose, guar gum, etc.) and a lubricant (for example talc, magnesium stearate, polyethylene-6000, etc.) are added to the active principle(s) and the mixture obtained is then tabletted. If necessary, the tablets can be coated via the known techniques, in order to mask the taste (for example with cocoa powder, mint, borneol, cinnamon powder, etc.) or to allow enteric dissolution or to allow sustained release of the active principles. The coating products that can be used are, for example, ethylcellulose, hydroxymethylcellulose, polyoxyethylene glycol, cellulose acetophthalate, hydroxypropylmethylcellulose phthalate and Eudragit® (methacrylic acid/acrylic acid copolymer) or Opadry® (hydroxypropylmethylcellulose+macrogol+titanium oxide+lactose monohydrate). Pharmaceutically acceptable colorants can also be added (for example yellow iron oxide, red iron oxide, quinoline yellow lake, etc.). Pharmaceutical forms, such as tablets, powders, sachets and gel capsules can be used for oral administration.

The liquid pharmaceutical forms for oral administration comprise solutions, suspensions and emulsions. The aqueous solutions can be obtained by dissolving the active principles in water, followed by addition of flavourings, colorants, stabilisers and thickeners, if necessary. In order to improve the solubility, it is possible to add ethanol, propylene glycol or other pharmaceutically acceptable non-aqueous solvents. The aqueous suspensions for oral use can be obtained by dispersing the finely divided active principles in water with a viscous product, such as natural or synthetic gums, resins, methylcellulose or sodium carboxymethylcellulose.

The pharmaceutical forms for injection can be obtained, for example, according to the following process: the active principle(s) is (are) dissolved, suspended or emulsified either in an aqueous medium (for example distilled water, physiological saline, Ringer's solution, etc.) or in an oily medium (for example a plant oil, such as olive oil, sesame seed oil, cottonseed oil, corn oil, etc. or propylene glycol), with a dispersant (for example Tween 80, HCO 60 (Nikko Chemicals), polyethylene glycol, carboxymethylcellulose, sodium alginate, etc.), a preserving agent (for example methyl para-hydroxybenzoate, propyl para-hydroxybenzoate, benzyl alcohol, chlorobutanol, phenol, etc.), an isotonic agent (for example sodium chloride, glycerol, sorbitol, glucose, etc.) and also other additives. If so desired, a solubilising agent (for example sodium salicylate, sodium acetate, etc.) or a stabiliser (for example human serum albumin) can be added.

A pharmaceutical form for external use can be obtained from a solid, semi-solid or liquid composition comprising the active principle(s). For example, to obtain a solid form, the active principle(s), alone or mixed with excipients (for example lactose, mannitol, starch, microcrystalline cellulose, sucrose, etc.) and a thickener (for example natural gums, cellulose derivatives, acrylic polymers, etc.) are treated so as to transform them into powder. The liquid pharmaceutical compositions are prepared in substantially the same manner as the forms for injection as indicated above. The semi-solid pharmaceutical forms are preferentially in the form of an aqueous or oily gel or in the form of an ointment. These compositions may optionally comprise a pH regulator (for example carbonic acid, phosphoric acid, citric acid, hydrochloric acid, sodium hydroxide, etc.) and a preserving agent (for example para-hydroxybenzoic acid esters, chlorobutanol, benzalkonium chloride, etc.), and also other additives.

The pharmaceutical compositions according to the present invention are useful for the prevention of or treating diabetes, insulin resistance, pathologies associated with insulin resistance syndrome (syndrome X), and obesity.

Insulin resistance is characterised by a reduction in the action of insulin (cf. *Presse Médicale*, 26(14), (1997), 671-677) and is involved in many pathological conditions, such as diabetes and more particularly non-insulin-dependent diabetes (type II diabetes or NIDDM), dyslipidaemia, obesity, arterial hypertension, and also certain cardiac, microvascular and macrovascular complications, for instance atherosclerosis, retinopathy and neuropathy.

In this respect, reference will be made, for example, to *Diabetes*, 37, (1988), 1595-1607; *Journal of Diabetes and its complications*, 12, (1998), 110-119; *Horm. Res.*, 38, (1992), 28-32, or to the book "*Uncomplicated Guide to Diabetes Complications*", Marvin E. Levin et al., 2002 which covers the complications of diabetes and of its effects on the kidneys, the heart, the eyes, the blood vessels and the nerves. More particularly, as regards neuropathy, reference will be made to *Cur. Opin. Investig. Drugs*, 7, (2006), 324-337.

The aim of the present invention is to propose a pharmaceutical composition comprising at least one compound of the formula (1) or (1') for significantly improving the condition of a diabetic patient.

The pharmaceutical compositions of the invention especially have hypoglycaemiant activity.

The compounds of the formula (1) or (1') are therefore useful in the treatment of pathologies associated with hyperglycaemia.

In this context, the effective doses and posologies for administration of the compounds of the invention, intended for the prevention of and treating a disorder or condition caused by or associated with modulation of AMPK activity, depends on a great many factors, for example on the nature of the compound, the size of the patient, the desired aim of the treatment, the nature of the pathology to be treated, the specific pharmaceutical composition used, and the observations and conclusions of the treating physician.

For example, in the case of an oral administration, for example of a tablet or a gel capsule, a suitable posology of the compounds is between about 0.1 mg/kg and about 100 mg/kg of body weight per day, preferably between about 0.5 mg/kg and about 50 mg/kg of body weight per day and more preferentially between about 1 mg/kg and about 10 mg/kg of body weight per day.

If representative body weights of 10 kg and 100 kg are considered, in order to illustrate the daily oral dosage range that can be used and as described above, suitable dosages of the compounds of the formula (1) or (1') will be between about 1-10 mg and 1000-10 000 mg per day, preferably between about 5-50 mg and 500-5000 mg per day and preferentially between 10-100 mg and 100-1000 mg per day of active material comprising a compound of the formula (1) according to the invention.

These dosage ranges represent the total amounts of active material per day for a given patient. The number of administrations per day for which a dose is administered may vary within wide proportions as a function of pharmacokinetic and pharmacological factors, such as the half-life of the active material, which reflects its rate of catabolism and of clearance, and also the minimum and optimum levels of the said active material reached in blood plasma or other body fluids of patients and which are required for therapeutic efficacy.

Many other factors should also be considered when deciding upon the number of daily administrations and the amount of active material that should be administered in a single intake. Among these other factors, and not the least of which, is the individual response of the patient to be treated.

The examples that follow illustrate the invention without, however, limiting it. The starting materials used are known products or products prepared according to known procedures.

The percentages are expressed on a weight basis, unless otherwise mentioned.

The compounds were especially characterised via the following analytical techniques:

NMR: The NMR spectra were obtained using a Brüker Advanced DPX 200 MHz NMR spectrometer or a Brüker Advanced DPX 500 MHz NMR spectrometer.

Mass: The masses were determined by HPLC coupled to an Agilent 1100 Series mass detector.

Melting point: The melting points (m.p.) were measured on a Köfler Leica VMBH block.

ABBREVIATIONS USED

NMR: Nuclear Magnetic Resonance;
MS: Mass Spectrum;
m.p.: melting point;
Yld: Yield;
DMSO: Dimethyl sulfoxide
DMF: Dimethylformamide;
THF: Tetrahydrofuran;
TBDMS: tert-Butyldimethylsilyl;
s: singlet;
d: doublet;
t: triplet;
q: quartet;
o: octet;
m: complex peak.

The chemical shifts δ are expressed in ppm.

Compounds of the Formula (1A)

A) Preparation of the Amines of the Formula (5A)

The amines (5A) are obtained according to the reaction scheme below:

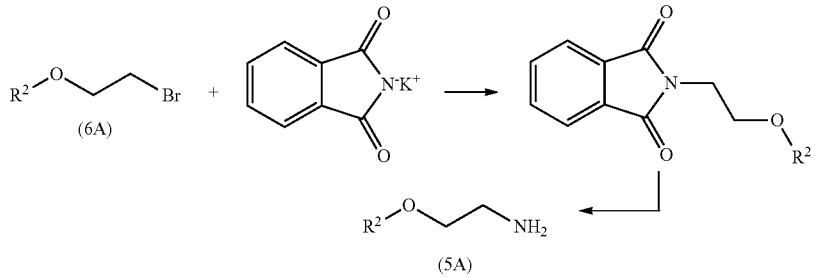

I) Preparation of the Compounds of the Formula (7A)

Amine (7A)-1: 2-(2-(4-fluorophenoxy)ethyl)isoindole-1,3-dione ($R^2$=4-fluorophenyl)

A mixture of 5 g (22.8 mmol) of 1-(2-bromoethoxy)-4-fluorobenzene (6A) and 4.23 g of potassium phthalimide (22.8 mmol) in 21 ml of DMF is heated for 1 hour (Oil bath temperature=100° C.).

When the medium has cooled to room temperature, a solution of saturated sodium chloride (NaCl) (about 150 ml) and of ethyl acetate (about 100 ml) is added.

After separation of the phases by settling, the aqueous phase is extracted with 3×80 ml of ethyl acetate and the combined organic phases are washed with 2×80 ml of NaCl and 2×80 ml of water.

The organic phase is dried over magnesium sulfate ($MgSO_4$) and concentrated.

6.20 g of a white solid are obtained.
Yld: 95%
m.p.=120° C.
$^1$H NMR (DMSO δ in ppm): 4.12 (t, 2H); 4.36 (t, 2H); 7.08 (d, 2H); 7.25 (t, 2H); 8.03 (s, 4H).

Purity=98%
MS (APCI) m/z: 286 [M+H]+
The following were similarly prepared:

Amine (7A)-2: 2-(2-(4-cyanophenoxy)ethyl)isoindole-1,3-dione

Yld: 100%
m.p.=186° C.
¹H NMR (DMSO δ in ppm): 4.04 (t, 2H); 4.20 (t, 2H); 6.82 (d, 2H); 7.44 (d, 2H); 7.76 (s, 2H); 7.77 (s, 2H).
Purity=92%
MS (APCI) m/z: 293 [M+H]+

Amine (7A)-3: methyl 4-[2-(1,3-dihydroisoindol-2-yl)ethoxy]benzoate

Yld: 93%
m.p.=127° C.
¹H NMR (DMSO δ in ppm): 3.75 (s, 3H); 3.94 (t, 2H); 4.26 (t, 2H); 6.97 (d, 2H); 7.83 (m, 6H).
Purity=98%
MS (APCI) m/z: 326 [M+H]+

II) Preparation of the Compounds of the Formula (5A)

Amine (5A)-1: (4-fluorophenoxy)ethylamine 60 g of the fluoro derivative (7A)-1 (210 mmol) were heated at reflux with 1.1 equivalents of hydrazine (11.2 ml) in 500 ml of absolute ethanol, with stirring for 3 hours, in a one-litre three-necked flask.

When hot, the medium becomes pale yellow and clear, and then opacifies again (about 30 minutes after the start of refluxing) and becomes white.

The ethanol is evaporated off under vacuum and 200 ml of 1N hydrochloric acid (HCl) are added to the 81.67 g of remaining white solid, to pH 1.

The insoluble matter (phthalide hydrazide) is filtered off and washed with water.

⅔ of the solvent are evaporated off under vacuum and the remaining material is then frozen and freeze-dried overnight.
32 g of white crystals are obtained.
Yld: 80%
m.p.=192-194° C. (hydrochloride)
¹H NMR (DMSO δ in ppm): 3.01 (t, 2H); 4.0 (t, 2H); 6.84 (t, 2H); 6.98 (t, 2H); 8.21 (s, 3H).
Purity=100%
MS (APCI) m/z: 194 [M+H]+
The following were similarly prepared:

Amine (5A)-2: 4-(2-aminoethoxy)benzonitrile

Yld: 80%
m.p.=260° C. (hydrochloride)
¹H NMR (DMSO δ in ppm): 3.26 (t, 2H); 4.33 (t, 2H); 7.16 (d, 2H); 7.87 (d, 2H); 8.40 (s, 3H).
Purity=100%
MS (APCI) m/z: 199 [M+H]+

Amine (5A)-3: methyl 4-(2-aminoethoxy)benzoate

Yld: 77%
m.p.=230° C. (hydrochloride)
¹H NMR (DMSO δ in ppm): 3.30 (t, 2H); 3.69 (s, 3H); 4.18 (t, 2H); 6.97 (d, 2H); 7.81 (d, 2H); 8.33 (s, 3H).
Purity=100%
MS (APCI) m/z: 232 [M+H]+

B) Preparation of the Malonamides (2A)

Malonamide (2A)-1: Ethyl ester of 3-[[2-(4-fluorophenoxy)ethyl]amino]-3-oxo-N-[(phenylmethoxy)carbonyl]alanine 2-(4-Fluorophenoxy)ethylamine (5A-1) in hydrochloride form is dissolved in water and basified with 1N sodium hydroxide (NaOH) to basic pH, and then extracted with ether. The free amine is thus obtained (yield=74%).

The malonate monoester (O) (7.5 g), the amine (5A)-1 (4.14 g) in ethanolic solution (30%) and hydroxybenzotriazole (HOBT) (3.97 g) in 70 ml of THF are placed in a 500 ml three-necked flask.

After complete dissolution, the whole is cooled to −7° C. and DCC (5.5 g) diluted in 30 ml of THF is then added dropwise over 30 minutes.

The mixture is allowed to warm to room temperature and is then left stirring for 19 hours. At room temperature, the medium becomes cloudy (white precipitate).

The precipitate (dicyclohexyl urea) is filtered off and concentrated to dryness. 15.77 g of a beige-coloured solid are obtained.

This crude solid is taken up in ethyl acetate (400 ml) and washed with:
HCl 1N (150 ml)
saturated sodium hydrogen carbonate solution (NaHCO₃) (150 ml)
saturated NaCl solution (150 ml)
water (150 ml).

After drying over MgSO₄ and evaporating off the solvent, 9.34 g of a beige-coloured solid are obtained.
Yld: 84%
m.p.=120° C.
¹H NMR (DMSO δ in ppm): 1.08 (s, 3H); 3.41 (t, 2H); 3.93 (t, 2H); 4.07 (q, 2H); 6.89 (t, 2H); 7.08 (t, 2H); 7.31 (s, 4H); 7.83 (s, 1H); 8.60 (t, 1H).
Purity=67%
MS (APCI) m/z: 419 [M+H]+
The following compounds are prepared according to similar processes

Malonamide (2A)-2: Ethyl ester of 3-[[2-(phenoxy)ethyl]amino]-3-oxo-N-[(phenylmethoxy)carbonyl]alanine Yld=71%
m.p.=85° C.
¹H NMR (DMSO δ in ppm): 1.15 (t, 3H); 3.42 (t, 2H); 4.11 (m, 4H); 4.99 (d, 1H); 5.10 (s, 2H); 6.97 (s, 3H); 7.39 (s, 7H).
Purity=99%
MS (APCI) m/z: 401 [M+H]+

Malonamide (2A)-3: Ethyl ester of 3-[[2-(4-cyanophenoxy)ethyl]amino]-3-oxo-N-[(phenylmethoxy)carbonyl]alanine Yld=68%
m.p.=142-144° C.
¹H NMR (DMSO δ in ppm): 0.97 (complex peak, 3H); 3.26 (t, 2H); 3.91 (t, 4H); 4.25 (t, 2H); 6.93 (d, 2H); 7.16 (s, 5H); 7.58 (s, 1H); 7.67 (s, 1H).
Purity=97%
MS (APCI) m/z: 426 [M+H]+

Malonamide (2A)-4: Ethyl ester of 3-[[2-(4-methoxycarbonylphenoxy)ethyl]amino]-3-oxo-N-[(phenylmethoxy)carbonyl]alanine Yld=79%
m.p.=102° C.
¹H NMR (DMSO δ in ppm): 1.43 (t, 3H); 3.59 (s, 1H); 3.76 (t, 2H); 4.04 (s, 3H); 4.30 (m, 4H); 5.11 (s, 1H); 5.29 (s, 2H); 7.26 (d, 2H); 7.59 (s, 5H); 8.13 (d, 2H); 8.90 (t, 1H).
Purity=97%
MS (APCI) m/z: 459 [M+H]⁺

C) Preparation of the Malonamides (3A)

Malonamide (3A)-1: phenylmethyl [1-(aminocarbonyl)-2-[[2-(phenoxy)ethyl]-amino]-2-oxoethyl]carabamate The amide (2A)-2 (6 g; 15 mmol) is dissolved in methanol (60 ml) in a 250 ml round-bottomed flask.
32% aqueous ammonia (25 ml) are then added and the mixture is stirred at room temperature for 24 hours.
The solvent is evaporated off. The residue obtained (beige-coloured solid) is taken up in isopropyl ether and filtered off. After drying, 5.6 g of a white solid are obtained.
Yld=100%
m.p.=133° C.
¹H NMR (DMSO δ in ppm): 3.30 (m, 2H); 3.83 (t, 2H); 4.47 (d, 1H); 4.90 (s, 2H); 6.78 (d, 3H); 7.20 (s, 8H); 8.22 (m. 1H).
Purity=100%
MS (APCI) m/z: 372 [M+H]⁺
The following compounds were prepared in a similar manner:

Malonamide (3A)-2: phenylmethyl [1-(aminocarbonyl)-2-[[2-(4-fluorophenoxy)ethyl]amino]-2-oxoethyl]carbamate Yld=83%
m.p.=138° C.
¹H NMR (DMSO δ in ppm): 3.34 (s, 2H); 3.85 (s, 2H); 4.55 (s, 1H); 4.93 (s, 2H); 6.84 (s, 3H); 6.99 (t, 4H); 7.24 (s, 5H); 8.22 (s. 1H).
Purity=71%
MS (APCI) m/z: 390 [M+H]⁺

Malonamide (3A)-3: phenylmethyl [1-(aminocarbonyl)-2-[[2-(4-cyanophenoxy)ethyl]amino]-2-oxoethyl]carabamate Yld=62%
m.p.=162° C.
¹H NMR (DMSO δ in ppm): 3.56 (d, 2H); 4.15 (d, 1H); 4.71 (d, 2H); 5.10 (s, 2H); 7.13 (d, 3H); 7.41 (s, 4H); 7.79 (d, 2H); 8.42 (t, 1H).
Purity=92%
MS (APCI) m/z: 397 [M+H]⁺

Malonamide (3A)-4: phenylmethyl [1-(aminocarbonyl)-2-[[2-(4-methoxycarbonyl phenoxy)ethyl]amino]-2-oxoethyl]carabamate Yld=53%
m.p.=148° C.
¹H NMR (DMSO δ in ppm): 3.37 (d, 2H); 3.70 (s, 3H); 3.98 (t, 2H); 4.55 (d, 1H); 4.93 (s, 2H); 6.91 (d, 2H); 7.25 (s, 8H); 7.82 (d, 2H); 8.25 (t, 1H).
Purity=96%
MS (APCI) m/z: 430 [M+H]⁺

D) Preparation of the Malonamides (4A)

Malonamide (4A)-1:
2-amino-N-[2-(4-fluorophenoxy)ethyl]malonamide

The amine (3A)-2 (3 g; 7.7 mmol) is dissolved in methanol (170 ml) in a 500 ml conical flask.
After total dissolution, 300 mg of wet activated palladium (Pd) (10%) on charcoal are added and the medium is then flushed with argon while stopping the stirring.
Once the conical flask has been rendered inert, the argon is replaced with hydrogen.
The mixture is stirred again for 1 hour.
Once the hydrogenation is complete, stirring is stopped to flush the medium with argon, and the contents of the conical flask are then filtered through a Clarcel filter, and the methanol is concentrated.
2.05 g of a white solid remain.
Yld=53%
m.p.=148° C.
¹H NMR (DMSO δ in ppm): 3.51 (d, 2H); 4.01 (t, 2H); 7.14 (s, 5H); 7.34 (s, 2H); 8.37 (s, 1H).
Purity=65%
MS (APCI) m/z: 256 [M+H]⁺
The following compounds were prepared in a similar manner:

Malonamide (4A)-2:
2-Amino-N-[2-phenoxyethyl]malonamide

Yld=64%
m.p.=140-142° C.
¹H NMR (DMSO δ in ppm): 2.35 (s, 2H); 3.31 (d, 2H); 3.84 (t, 2H); 4.53 (d, 1H); 6.79 (d, 2H); 7.18 (s, 2H); 7.21 (s, 1H); 8.24 (t, 1H).
Purity=94%
MS (APCI) m/z: 238 [M+H]⁺

Malonamide (4A)-3:
2-amino-N-[2-(4-cyanophenoxy)ethyl]malonamide

Yld=94
m.p.=138° C.
¹H NMR (DMSO δ in ppm): 2.29 (d, 2H); 3.29 (t, 2H); 3.69 (t, 1H); 3.89 (q, 2H); 6.87 (d, 2H); 7.51 (d, 2H); 8.28 (s, 2H).
Purity=100%
MS (APCI) m/z: 263 [M+H]⁺

Malonamide (4A)-4: methyl 4-[2-(2-amino-2-carbamoylethanoylamino)ethoxy]benzoate Yld=44%
m.p.=157° C.
¹H NMR (DMSO δ in ppm): 2.08 (t, 2H); 3.18 (m, 5H); 3.34 (t, 2H); 3.93 (t, 1H); 6.85 (d, 2H); 7.25 (s, 2H); 7.72 (d. 2H); 8.13 (t, 1H).

Purity=100%
MS (APCI) m/z: 296 [M+H]$^+$

E) Preparation Des Imidazoles (1A$_{OH}$)

Example 1

1-[2-(4-fluorophenoxy)ethyl]-5-hydroxy-1H-imidazole-4-carboxamide

The reagents (1 eq. of 2-amino-N-[2-(4-fluorophenoxy)ethyl]malonamide 3 per 5 eq. of ethyl orthoformate) are placed in a 100 ml three-necked flask equipped with a condenser and a calcium chloride (CaCl$_2$) guard tube, in refluxing absolute ethanol with a catalytic amount of para-toluenesulfonic acid (PTSA), for 2 hours 30 minutes.
Oil bath temperature=110° C.
Reaction medium temperature=80° C.
After cooling to room temperature, the precipitate formed (green solid) is isolated on a sinter funnel and dried (270 mg). The filtrate also comprising the expected product is concentrated to dryness: 2 g of a green solid (total 2.27 g) are obtained.
Yld=96%
m.p.=204° C.
$^1$H NMR (DMSO δ in ppm): 3.72 (t, 2H); 4.14 (t, 2H); 7.20 (m, 4H); 8.05 (s, 1H); 12.83 (s, 1H).
Purity=100%
MS (APCI) m/z: 266 [M+H]$^+$
The following compounds were prepared according to a similar process:

Example 2

5-hydroxy-1-(2-phenoxyethyl)-1H-imidazole-4-carboxamide

Yld=53%
m.p.=192° C.
$^1$H NMR (DMSO δ in ppm): 3.26 (t, 2H); 3.78 (t, 2H); 6.73 (s, 2H); 7.12 (s, 5H); 7.31 (s, 1H).
Purity=99%
MS (APCI) m/z: 248 [M+H]$^+$ Example 3

1-[2-(4-cyanophenoxy)ethyl]-5-hydroxy-1H-imidazole-4-carboxamide

Yld=35%
m.p.=190° C.
$^1$H NMR (DMSO δ in ppm): 3.96 (t, 2H); 4.27 (t, 2H); 7.05 (m, 4H); 7.69 (d, 2H); 8.08 (s, 1H).
Purity=91%
MS (APCI) m/z: 273 [M+H]$^+$ Example 4 methyl 4-[2-(4-carbamoyl-5-hydroxyimidazol-1-yl)ethoxy]benzoate

Yld=35%
m.p.=190° C.
$^1$H NMR (DMSO δ in ppm): 3.82 (s, 3H); 4.17 (t, 2H); 4.34 (t, 2H); 7.08 (m, 4H); 7.94 (d, 2H); 8.22 (s, 1H).

Purity=99%
MS (APCI) m/z: 306 [M+H]$^+$

Compounds of the Formula (1B)

A) Preparation of the imino ether (3B-1: R$^4$=ethyl): diethyl 2-methoxy-methyleneaminomalonate The amine of ethyl aminomalonate hydrochloride is freed via the stoichiometric addition of 1N NaOH (0.13 mol=130 ml) followed by extraction with CH$_2$Cl$_2$. 17 g of a sparingly coloured oil are obtained (yield=82%).
516 ml of triethyl orthoformate are refluxed with a catalytic amount of trifluoroacetic acid (CF$_3$COOH) (640 μl) in a one-litre three-necked flask under argon, equipped with a condenser and a thermometer.
Oil bath temperature=155° C.
Reaction medium temperature=130° C.
At reflux, the amine (18.1 g; 103.3 mmol) in 100 ml of acetonitrile is added dropwise over 5 hours.
After cooling to room temperature, the solvent is evaporated off. 25.06 g of a green oil, which is used without further processing, are obtained.
Yld=100% (crude)
$^1$H (CDCl$_3$ δ in ppm): 1.44 (m, 9H); 3.72 (s, 1H); 4.40 (q, 6H); 7.8 (s, 1H).
Purity=90%

B) Preparation of the Imidazoles (1B$_{OH}$)

Example 5 ethyl 5-hydroxy-1-(2-phenoxyethyl)-1 imidazole-4-carboxylate 2.1 equivalents (6.22 g; 45.4 mmol) of 2-phenoxyethylamine diluted in 70 ml of ethyl acetate are introduced dropwise into a three-necked flask containing 5 g (21.6 mmol) of imino ether and 80 ml of ethyl acetate, placed under argon. The reaction medium is stirred for 24 hours at room temperature. A precipitate forms.
After filtering off and drying, 2.23 g of the salt of ethyl 5-hydroxy-1-(2-phenoxyethyl)-1H-imidazole-4-carboxylate with 2-phenoxyethylamine are isolated (formula (1B$_O$)):
Yld=25%
m.p.=150° C.
$^1$H NMR (DMSO δ in ppm): 1.05 (t, 3H); 3.93 (m, 6H); 6.80 (m, 5H); 7.15 (s, 1H); 7.69 (s, 1H).
Purity=97%
MS (APCI) m/z: 277 [M+H]$^+$; 138 [M+H]$^+$ phenoxyethylamine
The acid form (formula (1B$_{OH}$)) is freed by adding 4.83 ml (1 eq) of 1N HCl in a flask containing 2 g of salt (1B$_O$) described above in 20 ml of water, followed by maintaining the stirring overnight at room temperature.
After filtering off and drying, 0.938 g of a white solid is isolated.
Yld=70%
m.p.=186° C.
Compounds (1B$_{OH}$) and (1B$_R$) below are prepared according to a similar process.

Example 6 ethyl 5-hydroxy-1-[2-(-4-cyanophenoxy)ethyl]-1H-imidazole-4-carboxylate

Characteristics of the Salt 2-(4-cyanophenoxy)ethylammonium 3-[2-(4-cyanophenoxy)ethyl]-5-ethoxycarbonyl-3H-imidazol-4-ate (formula (1B'):

Yld=8%
m.p.=147° C.
¹H NMR (DMSO δ in ppm): 1.19 (t, 3H); 4.05 (m, 6H); 7.12 (m, 2H); 7.76 (d, 3H); 8.05 (s, 1H).
Purity=60%
MS (APCI) m/z: 302 [M+H]⁺; 163 [M+H]⁺ phenoxyethylamine
Characteristics of the compound of Example 6:
Yld=77%
m.p.=190° C.

Example 7 ethyl 5-hydroxy-1-[2-(-4-fluorophenoxy)ethyl]-1H-imidazole-4-carboxylate

Characteristics of the salt 2-(4-fluorophenoxy)ethylammonium 5-ethoxycarbonyl-3-[2-(4-fluorophenoxy)ethyl]-3H-imidazol-4-ate (formula (1B')):
Yld=31%
m.p.=126° C.
¹H NMR (DMSO δ in ppm): 1.23 (t, 3H); 4.13 (m, 6H); 7.14 (m, 4H); 7.32 (s, 1H).
Purity=97%
MS (APCI) m/z: 295 [M+H]⁺; 156 [M+H]⁺ phenoxyethylamine
Characteristics of the compound of Example 7:
Yld=88%
m.p.=200° C.

Example 8 ethyl 5-hydroxy-1-{2-[-4(methoxycarbonyl)phenoxy]ethyl}-1H-imidazole-4-carboxylate Characteristics of the salt 2-(4-methoxycarbonylphenoxy)ethylammonium 5-ethoxycarbonyl-3-[2-(4-methoxycarbonylphenoxy)ethyl]-3H-imidazol-4-ate:
Yld=39%
m.p.=152° C.
¹H NMR (DMSO δ in ppm): 0.99 (t, 3H); 3.64 (s, 3H); 4.01 (m, 6H); 6.84 (m, 2H); 7.27 (s, 1H); 7.71 (m, 2H).
Purity=57%
MS (APCI) m/z: 335 [M+H]⁺; 196 [M+H]⁺ phenoxyethylamine
Characteristics of the compound of Example 8:
Yld=88%
m.p.=202° C.

Example 9 ethyl 1-benzyl-5-methoxy-1H-imidazole-4-carboxylate 5.39 g (22 mmol) of ethyl 1-benzyl-5-hydroxy-1H-imidazole-4-carboxylate (prepared according to the process described for the preparation of compounds 2B) and 12.14 g (88 mmol; 4 eq.) of potassium carbonate are placed in 150 ml of DMF in a round-bottomed flask. The reaction medium is brought to 60° C. and 2.1 ml of methyl iodide (34 mmol; 1.5 eq.) are then added dropwise. After 2 hours at 60° C., the medium is cooled, poured into brine (water+NaCl) and extracted several times with ether. The organic phases are combined and, after drying, are evaporated. A viscous red oil (4 g) is isolated and taken up in an isopropyl ether/ethyl acetate mixture (80/20). The precipitate obtained is then filtered off and dried to give 1.59 g of a cream-white solid.

Yld=28%
m.p.=127-128° C.
¹H (CDCl₃ δ in ppm): 0.35 (t, 3H); 3.85 (s, 3H); 4.30 (quartet, 2H); 4.92 (s, 2H); 7.32 (s, 5H); 7.85 (s, 1H).
Purity=98.5%
MS (APCI) m/z: 261 [M+H]⁺

Compounds of the Formulae $(1C_{OH})$ and $(1C_R)$

A) Preparation of 2-Bromomalonamide (Compound (2C))

A solution of bromine in acetic acid (78 g, i.e. 25 ml in 200 ml) is added dropwise over 5 hours to 50 g of malonamide (0.49 mol) dissolved in 300 ml of acetic acid at 60° C., with stirring and while maintaining the temperature at 60° C. The medium decolorises instantaneously. It turns yellow after 2 hours 30 minutes of addition.

After concentrating and drying, 90.94 g of a pale pink solid are obtained. This solid is triturated from 95% ethanol and then suction-filtered to give 79.24 g of 2-bromomalonamide.
Yld=89%.
m.p.=178° C.
¹H NMR (DMSO δ in ppm): 4.67 (s, 1H); 7.59 and 7.68 (s, 2H).
Purity (HPLC)=99%
MS (APCI) m/z: 182 [M+H]⁺

B) Preparation of the Aminomalonamides (3C)

Aminomalonamide (3C)-1:
2-(4-Fluorobenzylamino)malonamide 2 equivalents of triethylamine (15.3 ml) and 1 equivalent of 4-fluorobenzylamine (8.92 g) are added to 10 g of 2-bromomalonamide (55.25 mmol) dissolved in absolute ethanol.

The mixture is refluxed for 3 hours.

The mixture is soluble while hot (yellow solution).

After returning to room temperature and cooling the medium with a water/ice mixture, the precipitate formed is filtered off and then washed with a small amount of 95% ethanol. After drying, 11.82 g of a white solid are isolated.
Yld=99%.
m.p.=152-156° C.
¹H NMR (DMSO δ in ppm): 3.77 (d, 1H); 3.80 (m, 2H); 7.51 (m, 2H aromatic); 7.59 (m, 2H more deshielded aromatic).
Purity=89%
MS (APCI) m/z: 226.2 [M+H]⁺

The following 2-aminomalonamides (3C) were prepared according to a similar process:

Aminomalonamide (3C)-2:
2-[2-(4-Fluorophenoxy)ethylamino]malonamide

Yld=80%.
m.p.=116° C.
¹H NMR (DMSO δ in ppm): 3.05 (t, 2H); 3.57 (s, 1H); 3.91 (s, 1H); 4.23 (t, 2H); 7.18 (m, 2H); 7.34 (t, 2H); 7.61 (d, 4H).
Purity=93%
MS (APCI) m/z: 256 [M+H]⁺

Aminomalonamide (3C)-3:
2-[2-(4-cyanophenoxy)ethylamino]malonamide

Yld=33%.
m.p.=130° C.

¹H NMR (DMSO δ in ppm): 2.77 (t, 1H); 3.27 (t, 2H); 3.62 (d, 1H); 4.03 (t, 2H); 7.03 (d, 2H); 7.69 (d, 6H).
Purity=99.9%
MS (APCI) m/z: 263 [M+H]⁺

Aminomalonamide (3C)-4: methyl 4-{2-[(1,1-dicarbamoylmethyl)amino]ethoxy}benzoate Yld=79%.
m.p.=168° C.
¹H NMR (DMSO δ in ppm): 3.08 (t, 2H); 3.95 (s, 1H); 4.02 (s, 3H); 4.33 (t, 2H); 7.24 (d, 2H); 7.66 (d, 4H); 8.14 (d, 2H).
Purity=95%
MS (APCI) m/z: 296 [M+H]⁺

Aminomalonamide (3C)-5: 2-(4-chlorobenzylamino)malonamide

Yld=99%
m.p.=150-153° C.
¹H NMR (DMSO δ in ppm): 3.77 (d, 1H); 3.80 (m, 2H); 7.51 (m, 2H aromatic); 7.59 (m, 2H more deshielded aromatic).
Purity=69.2%
MS (APCI) m/z: 242.1 [M+H]⁺

Aminomalonamide (3C)-6: 2-[4-(ethoxycarbonyl)benzylamino]malonamide

Yld=77.2%
m.p.=204-206° C.
¹H NMR (DMSO δ in ppm): 1.2 (t, 3H); 3.96 (m, 2H); 4.52 (q, 2H); 7.75 (d, 2H); 8.12 (d, 2H).
Purity=99%
MS (APCI) m/z: 280.2 [M+H]⁺

Aminomalonamide (3C)-7: 2-phenylaminomalonamide

Yld=50%
m.p.=134-138° C.
¹H NMR (DMSO δ in ppm): 4.21 (d, 2H); 6.25-7.75 (m, 5H aromatic).
Purity=78.5%
MS (APCI) m/z: 194.2 [M+H]⁺

C) Preparation of the Imidazoles (1C)

Example 10

5-hydroxy-3-(4-fluorobenzyl)imidazole-4-carboxamide 16.05 g (71.04 mmol) of 2-(4-fluorobenzylamino)malonamide are refluxed with 71 ml of triethyl orthoformate, i.e. 6 equivalents, and a catalytic amount of PTSA (250 mg) in 535 ml of absolute ethanol, in a round-bottomed flask placed under argon.
The reagent dissolves in the hot ethanol.
After refluxing for 3 hours, the reaction medium is cooled. The precipitate appears. It is filtered off and washed with 95% ethanol. A white solid (8.68 g) is isolated.
Yld=67.8%
m.p.=230-234° C.
¹H NMR (DMSO δ in ppm): 5.52 (s, 2H); 6.76 (broad s, H of the OH); 7.20 to 7.44 (m, 6H); 8.16 (s, 1H).
Purity=97.7%
MS (APCI) m/z: 236.2 [M+H]⁺
The following imidazole compounds (1C) were prepared according to a similar process.

Example 11

5-hydroxy-3(4-chlorobenzyl)imidazole 4-carboxamide

Yld=99%
m.p.=206-212° C.
¹H NMR (DMSO δ in ppm): 5.52 (s, 2H); 6.78 (broad s, H of the OH); 7.20 to 7.5 (m, 6H); 8.15 (s, 1H).
Purity=99%
MS (APCI) m/z: 252.1 [M+H]⁺

Example 12

5-hydroxy-3-[4-(ethoxycarbonyl)benzyl]imidazole-4-carboxamide

Yld=84.5%
m.p.=266-268° C.
¹H NMR (DMSO δ in ppm): 1.53 (s, 3H of the CH₃); 3.6 (s, 1H of the OH); 4.55 (q, 2H); 5.81 (s, 2H), 7.59 (d, 2H); 8.13 (d, 2H); 8.34 (s, 1H).
Purity=99.1%
MS (APCI) m/z: 288.2 [M−1]

Example 13

5-hydroxy-3-phenylimidazole-4-carboxamide

Yld=19%
m.p.=182° C.
¹H NMR (DMSO δ in ppm): 2.92 (s, 1H); 6.99 (broad s, 2H); 7.35 (m, 1H); 7.39 (m, 4H); 7.87 (s, 1H).
Purity=99%
MS (APCI) m/z: 202.2 [M−1]

Example 14

5-hydroxy-3-(2-phenoxyethyl)-3H-imidazole-4-carboxamide

Yld=86%.
m.p.=24° C.
¹H NMR (DMSO δ in ppm): 3.37 (1s, 2H); 4.21 (t, 2H); 4.53 (t, 2H); 6.87 (t, 3H); 7.21 (t, 2H); 7.94 (s, 1H); 11.85 (s, 1H).
Purity≧99%
MS (APCI) m/z: 248 [M+H]⁺

Example 15

3-[2-(4-fluorophenoxy)ethyl]-5-hydroxy-3H-imidazole-4-carboxamide

Yld=98%.
m.p.=230° C.
¹H NMR (DMSO δ in ppm): 4.32 (t, 2H); 4.65 (t, 2H), 7.00 (d, 2H); 7.15 (t, 2H); 7.46 (s, 1H); 8.07 (s, 1H).
Purity=100%
MS (APCI) m/z: 266 [M+H]⁺

Example 16

3-[2-(4-cyanophenoxy)ethyl]-5-hydroxy-3H-imidazole-4-carboxamide

Yld=82%.
m.p.=264° C.
$^1$H NMR (DMSO δ in ppm): insoluble
Purity=100%
MS (APCI) m/z: 273 [M+H]$^+$

Example 16b is methyl 4-[2-(5-carbamoyl-4-hydroxyimidazol-1-yl)ethoxy]-benzoate

Yld=77%.
m.p.=263° C.
$^1$H NMR (DMSO δ in ppm): 4.01 (s, 3H); 4.58 (t, 2H); 4.83 (t, 2H); 6.91 (s, 2H); 7.22 (d, 2H); 8.08 (d, 2H); 8.22 (s, 1H).
Purity=100%
MS (APCI) m/z: 306 [M+H]$^+$

Example 17

5-hydroxy-3-phenylimidazole-4-carboxamide

Yld=19%
m.p.=182° C.
$^1$H NMR (DMSO δ in ppm): 2.92 (s, 1H); 6.99 (broad s, 2H); 7.35 (m, 1H); 7.39 (m, 4H); 7.87 (s, 1H).
Purity=99%
MS (APCI) m/z: 202.2 [M−1]

Example 18

3-(4-aminobenzyl)-5-hydroxy-3H-imidazole-4-carboxamide 1 g (3.81 mmol) of 3-(4-nitrobenzyl)-5-hydroxy-3H-imidazole-4-carboxamide is placed in 30 ml of methanol with 100 mg of palladium-on-charcoal (51% water) in a hydrogenation flask. The medium is flushed with argon and then with hydrogen for 30 minutes with stirring. The medium is again flushed with argon and the catalyst is filtered off by suction. The solvent is evaporated off to give 0.710 g of a yellowish-white solid.
Yld=80%
m.p.=230-231° C.
$^1$H NMR (DMSO δ in ppm): 3.41 (broad s, 2H); 5.10 (broad s, 2H); 5.28 (s, 2H); 6.49 (d, 2H); 7.02 (d, 2H); 7.98 (s, 1H).
Purity=99%
MS (APCI) m/z: 233 [M+H]$^+$

D) Preparation of the Imidazoles (1C)

Example 19

3-(4-nitrobenzyl)-5-methoxy-3H-imidazole-4-carboxamide 3.93 g (15 mmol) of the derivative 3-(4-nitrobenzyl)-5-hydroxy-3H-imidazole-4-carboxamide are added to 80 ml of DMF in a three-necked flask under argon, followed by addition of 8.29 g (60 mmol; 4 eq.) of potassium carbonate. The stirred medium is maintained at 50° C. for 30 minutes and then cooled to room temperature. Methyl iodide (5.75 g; 40.5 mmol; 2.7 eq.) is then added.

The reaction medium is stirred for 12 hours at room temperature and is then poured into brine and extracted with ether. After drying and evaporation, 1.88 g of an orange solid are isolated and recrystallised from 95% ethanol to give 0.672 g of an orange solid.
Yld=16.2%
m.p.=201-203° C.
$^1$H NMR (DMSO δ in ppm): 3.85 (s, 3H); 5.3 (s, 2H); 7.33 (d+s, 3H); 8.16 (d, 2H).
Purity=99%
MS (APCI) m/z: 277 [M+H]$^+$

Example 20

3-(4-nitrobenzyl)-5-benzyloxy-3H-imidazole-4-carboxamide

This compound was prepared according to the procedure described in Example 19, benzyl bromide being used instead of methyl iodide.
Yld=37.6%
m.p.=193-195° C.
$^1$H NMR (DMSO δ in ppm): 5.33 (s, 2H); 5.57 (s, 2H); 6.46 (broad s, 2H); 7.28 (m, 8H); 8.09 (d, 2H).
Purity=99%
MS (APCI) m/z: 353 [M+H]$^+$

Compounds of the Formulae (1Ca) and (1Cb)

A) Preparation of (4C): 3-(4-nitrobenzyl)-5-(tert-butyldimethylsilanyloxy)-3H-imidazole-4-carboxamide 52.44 g (0.2 mol) of nitro compound (1C—NO$_2$) are placed in 400 ml of DMF in a three-necked flask under argon. The suspension is yellow. 38.58 g (0.256 mol) of tert-butyldimethylsilyl chloride are then added in a single portion. The temperature is 21° C.

35 g of imidazole (0.514 mol) dissolved in 150 ml of DMF are then added dropwise. The temperature rises to 27° C. The reaction medium is left for 3 hours 30 minutes at room temperature and then poured into 2 litres of brine and extracted several times with ether. After drying and evaporating off the solvent, 73 g of a yellow solid are obtained.
Yld=97%
m.p.=190-192° C.
$^1$H NMR (DMSO δ in ppm): 0.37 (s, 6H); 1.00 (s, 9H); 5.67 (s, 2H); 6 (broad s, 2H); 7.41 (d, 2H); 7.80 (s, 1H); 8.21 (d, 2H).
Purity=98%
MS (APCI) m/z: 377 [M+H]$^+$

B) Preparation of (5C): 3-(4-aminobenzyl)-5-(tert-butyldimethylsilanyloxy)-3H-imidazole-4-carboxamide 25 g of (5C) (66.4 mmol) are placed in a hydrogenation flask under argon, containing 1.8 l of methanol, followed by addition of 2.5 g of 10% palladium-on-charcoal (50% water). After stirring for 30 minutes under an atmosphere of hydrogen at ordinary pressure and at room temperature, the reaction medium is flushed with argon.

The catalyst is filtered off and the methanolic solution is evaporated to give 20 g of a white solid.

Yld=87%
m.p.=194-196° C.
¹H NMR (DMSO δ in ppm): 0.33 (s, 6H); 0.98 (s, 9H); 5.09 (s broad, 1H); 5.31 (s, 2H); 6.53 (d, 2H); 6.99 (d, 2H); 7.60 (s, 1H).
Purity=99%
MS (APCI) m/z: 347 [M+H]⁺

C) Preparation of the Imidazoles (1Ca)

Example 21

5-hydroxy-3-[4-(3-methoxybenzoylamino)benzyl]-3H-imidazole-4-carboxamide 1 g of silyl amine 3C (2.88 mmol) is placed in a round-bottomed flask under an atmosphere of nitrogen containing 15 ml of dry THF. 0.349 g (0.481 ml) of triethylamine (3.46 mmol, 1.2 eq.) is added, followed by addition of 0.492 g of 3-methoxybenzoyl chloride (0.1 eq.) dissolved in 5 ml of dry THF.

The reaction medium is stirred for 72 hours at room temperature. 25 ml of water and 1 ml of 1N HCl are then added. The mixture is stirred for 48 hours. The precipitate obtained is filtered off and washed with water and then with petroleum ether. After drying, 1.018 g of a white solid are obtained.
Yld=96.3%
m.p.=257-259° C.
¹H NMR (DMSO δ in ppm): 4.07 (s, 3H); 5.72 (s, 2H); 5.67 (s, 2H); 7.39-7.97 (m, 8H); 8.33 (s, 1H).
Purity=98.4%
MS (APCI) m/z: 367 [M+H]⁺

The imidazole compounds (1Ca$_{OH}$) below are prepared according to a similar process (purity greater than 90% determined by HPLC-mass).

Example 22

3-(4-acetylaminobenzyl)-5-hydroxy-3H-imidazole-4-carboxamide

Example 23

3-(4-benzoylaminobenzyl)-5-hydroxy-3H-imidazole-4-carboxamide

Example 24

3-[4-(cyclohexanecarbonylamino)benzyl]-5-hydroxy-3H-imidazole-4-carboxamide

Example 25

5-hydroxy-3-[4-(4-methoxybenzoylamino)benzyl]-3H-imidazole-4-carboxamide

Example 26

3-[4-(3,3-dimethylbutyrylamino)benzyl]-5-hydroxy-3H-imidazole-4-carboxamide

Example 27

5-hydroxy-3-[4-(4-fluorobenzoylamino)benzyl]-3H-imidazole-4-carboxamide

Example 28

5-hydroxy-3-{4-[(naphthalene-1-carbonyl)amino]benzyl}-3H imidazole-4-carboxamide

Example 29

3-[4-(3-cyclopentylpropionylamino)benzyl]-5-hydroxy-3H-imidazole-4-carboxamide

Example 30

3-{4-[2-(4-chlorophenyl)acetylamino]benzyl}-5-hydroxy-3H-imidazole-4-carboxamide

Example 31

5-hydroxy-3-[4-(4-chlorobenzoylamino)benzyl]-3H-imidazole-4-carboxamide

Example 32

3-(4-hexanoylaminobenzyl)-5-hydroxy-3H-imidazole-4-carboxamide

Example 33

5-hydroxy-3-[4-(2-fluorobenzoylamino)benzyl]-3H-imidazole-4-carboxamide

Example 34

5-hydroxy-3-[4-(4-methyl benzoylamino)benzyl]-3H-imidazole-4-carboxamide

Example 35

5-hydroxy-3-[4-(2-methoxybenzoylamino)benzyl]-3H-imidazole-4-carboxamide

Example 36

5-hydroxy-3-{4-[(naphthalene-2-carbonyl)amino]benzyl}-3H-imidazole-4-carboxamide

Example 37

5-hydroxy-3-{4-[2-(4-nitrophenyl)acetylamino]benzyl}-3H-imidazole-4-carboxamide

Example 38

5-hydroxy-3-[4-(2-phenylbutyrylamino)benzyl]-3H-imidazole-4-carboxamide

Example 39

3-[4-(2-furan-2-ylacetylamino)benzyl]-5-hydroxy-3H-imidazole-4-carboxamide

Example 40

5-hydroxy-3-[4-(2-thiophen-2-ylacetylamino)benzyl]-3H-imidazole-4-carboxamide

D) Preparation of the Imidazoles (1Cb)

Example 41

5-hydroxy-3-[4-(3-phenylureido)benzyl]-3H-imidazole-4-carboxamide 0.5 g of silyl amine 3C (1.44 mmol) is placed in a round-bottomed flask under a nitrogen atmosphere containing 10 ml of dry THF, followed by addition of 0.172 g (1.44 mmol; 1 eq.) of phenyl isocyanate in a single portion.

A precipitate forms after 5 hours 30 minutes of stirring at room temperature. The reaction medium is stirred for 29 hours. 10 ml of water and 1 ml of 1N HCl are then added. After stirring for a further 48 hours at room temperature, the solvent is evaporated off and the residue is taken up in a water-ice mixture. The precipitate is washed with water and then with petroleum ether.

After drying, 270 mg of a white solid are obtained.
Yld=53.2%
m.p.=232-235° C.
$^1$H NMR (DMSO δ in ppm): 5.47 (s, 2H); 7.05 (m, 1H); 7.25-7.45 (2×t, H); 8.25 (s, 1H); 8.60 (2s, 2H).
Purity=96.1%
MS (APCI) m/z: 352 [M+H]$^+$

Example 42

5-hydroxy-3-[4-ureidobenzyl]-3H-imidazole-4-carboxamide 0.187 g of sodium cyanide (24.7 mmol; 2 eq.) dissolved in 5 ml of water is added to a round-bottomed flask containing 10 ml of water and 0.5 g (14.4 mmol) of 3-(4-aminobenzyl)-5-(tert-butyldimethylsilanyloxy)-3H-imidazole-4-carboxamide, followed by dropwise addition of 10 ml of acetic acid over 5 minutes. The medium turns yellow. After stirring for 24 hours at room temperature, the solvent is evaporated off. 30 ml of water and 1 ml of 1N HCl are added to the residue and the resulting mixture is stirred for a further 24 hours at room temperature.

After filtering off, washing with water and drying, 330 mg of white solid are obtained.
Yld=83%
m.p.=243-244° C.
$^1$H NMR (DMSO δ in ppm): 5.45 (s, 2H); 7.25-7.60 (m, 5H); 8.10 (s, 1H); 8.60 (s, 1H).
Purity=99%
MS (APCI) m/z: 276 [H]$^+$ The following imidazole compounds (1Cb$_{OH}$) are prepared according to a process similar to that indicated for Example 41 (purity greater than 90% determined by HPLC-Mass).

Example 43

5-hydroxy-3-{4-[3-(4-methoxyphenyl)ureido]benzyl}-3H-imidazole-4-carboxamide

Example 44

5-hydroxy-3-{4-[3-(4-chlorophenyl)ureido]benzyl}-3H-imidazole-4-carboxamide

Example 45

3-[4-(3-cyclohexyl ureido)benzyl]-5-hydroxy-3H-imidazole-4-carboxamide

Example 46

3-[4-(3-cyclopentylureido)benzyl]-5-hydroxy-3H-imidazole-4-carboxamide

Example 47

5-hydroxy-3-[4-(3-naphthalen-1-ylureido)benzyl]-3H-imidazole-4-carboxamide

Example 48

5-hydroxy-3-[4-(3-naphthalen-2-ylureido)benzyl]-3H-imidazole-4-carboxamide

Example 49

5-hydroxy-3-{4-[3-(5,6,7,8-tetrahydronaphthalen-1-yl)ureido]benzyl}-3H-imidazole-4-carboxamide

Example 50

3-[4-(3-ethylureido)benzyl]-5-hydroxy-3H-imidazole-4-carboxamide

Example 51

3-[4-(3-benzylureido)benzyl]-5-hydroxy-3H-imidazole-4-carboxamide

Example 52

5-hydroxy-3-[4-(3-meta-tolylureido)benzyl]-3H-imidazole-4-carboxamide

Example 53

5-hydroxy-3-{4-[3-(3-methoxyphenyl)ureido]benzyl}-3H-imidazole-4-carboxamide

Example 54

3-{4-[3-(2-fluorobenzyl)ureido]benzyl}-5-hydroxy-3H-imidazole-4-carboxamide

Example 55

5-hydroxy-3-{4-[3-(2-methoxyphenyl)ureido]benzyl}-3H-imidazole-4-carboxamide

Example 56

5-hydroxy-3-{4-[3-(4-ethylphenyl)ureido]benzyl}-3H-imidazole-4-carboxamide

Example 57

5-hydroxy-3-{4-[3-(3-methylsulfanylphenyl)ureido]benzyl}-3H-imidazole-4-carboxamide

Example 58

5-hydroxy-3-{4-[3-(4-methylsulfanylphenyl)ureido]benzyl}-3H-imidazole-4-carboxamide

Example 59

5-hydroxy-3-[4-(3-indan-5-yl ureido)benzyl]-3H-imidazole-4-carboxamide

Example 60

5-hydroxy-3-{4-[3-(4-fluorophenyl)ureido]benzyl}-3H-imidazole-4-carboxamide

Example 61

5-hydroxy-3-{4-[3-(2-chlorophenyl)ureido]benzyl}-3H-imidazole-4-carboxamide

Example 62

5-hydroxy-3-{4-[3-(2-trifluoromethylphenyl)ureido]benzyl}-3H-imidazole-4-carboxamide

Example 63

5-hydroxy-3-{4-[3-(3-trifluoromethyl phenyl)ureido]benzyl}-3H-imidazole-4-carboxamide

Example 64

5-hydroxy-3-{4-[3-(4-trifluoromethyl phenyl)ureido]benzyl}-3H-imidazole-4-carboxamide

Example 65 ethyl 3-{3-[4-(5-carbamoyl-4-hydroxyimidazol-1-ylmethyl)phenyl]ureido}benzoate

Example 66 ethyl 4-{3-[4-(5-carbamoyl-4-hydroxyimidazol-1-ylmethyl)phenyl]ureido}benzoate

Example 67

4-{3-[4-(5-carbamoyl-4-hydroxyimidazol-1-ylmethyl)phenyl]ureido}benzoic acid

Example 68 ethyl 2-{3-[4-(5-carbamoyl-4-hydroxyimidazol-1-ylmethyl)phenyl]ureido}benzoate

Example 69 ethyl {3-[4-(5-carbamoyl-4-hydroxyimidazol-1-ylmethyl)phenyl]ureido}acetate

Example 70

3-{3-[4-(5-carbamoyl-4-hydroxyimidazol-1-ylmethyl)phenyl]ureido}benzoic acid 100 mg of ethyl 3-{3-[4-(5-carbamoyl-4-hydroxyimidazol-1-ylmethyl)phenyl]-ureido}benzoate (0.236 mmol), 5 ml of ethanol and 1 ml of water are placed in a round-bottomed flask. 0.472 ml of 1N NaOH (2 eq.) is added to the white suspension. The dissolution is instantaneous. The medium is maintained at 50° C. for 4 hours.

After evaporating off the solvent under vacuum, 10 ml of water and 0.472 ml of 1N HCl (2 eq.) are added. The white precipitate formed is stirred for 1 hour.

After filtering off, washing with water and drying, 83 mg of a white solid are isolated.

Yld=89% m.p.=218-220° C.

$^1$H NMR (DMSO δ in ppm): 5.49 (s, 2H); 7.29-7.75 (m, 8H); 8.13 (d, 2H); 9.25 (s, 1H); 12.38 (broad s, COOH).

Purity=99%
MS (APCI) m/z: 396 [H]+

O-Alkyl and O-acyl Compounds of (1Ca_R)

Example 71

5-methoxy-3-{4-[(naphthalene-1-carbonyl)amino]benzyl}-3H imidazole-4-carboxamide 200 mg (0.517 mmol) of 5-hydroxy-3-{4-[(naphthalene-1-carbonyl)amino]benzyl}-3H-imidazole-4-carboxamide are dissolved in 5 ml of dry DMF in a round-bottomed flask under argon. 285 mg (2.07 mmol; 4 eq.) of potassium carbonate are then added. After one hour at room temperature, 440 mg (3.1 mmol; 6 eq.) of methyl iodide are added. After stirring for 24 hours at room temperature, the reaction medium is poured into brine and a precipitate appears. After stirring for 20 minutes, the precipitate is filtered off and then washed with water. After drying, 72 mg of a white solid are obtained.
Yld=34.7%
m.p.=101-103° C.
$^1$H NMR (DMSO δ in ppm): 3.90 (s, 3H); 5.37 (s, 2H); 7.30-7.90 (m, 11H); 8.40-8.5 (m, 3H).
Purity=98%
MS (APCI) m/z: 400.43 [M+H]$^+$

Example 72

5-acetyloxy-3-[4-(4-acetylamino)benzyl]-3H-imidazole-4-carboxamide 262 mg (1.12 mmol) of 3-(4-aminobenzyl)-5-hydroxy-3H-imidazole-4-carboxamide are added to 10 ml of dry THF in a round-bottomed flask under argon. 250 mg of triethylamine (2.48 mmol; 2.2 eq.) and then 177 mg (2.25 mmol; 2 eq.) of acetyl chloride are added with stirring. The mixture is stirred for 12 hours at room temperature. The medium is evaporated and the residue is taken up in water. The solid formed is filtered off by suction and then washed with water and dried into give 25 mg of a white solid.
Yld=7%
m.p.=240-243° C.
$^1$H NMR (DMSO δ in ppm): 2.15 (s, 3H); 2.32 (s, 3H); 5.50 (s, 2H); 7.39 (dd, 4H); 8.02 (s, 1H).
Purity=99%
MS (APCI) m/z: 317 [M+H]$^+$

Biology

A) Experimental Protocol 25 mU of AMPK are incubated in the presence of different concentrations of AMP or of products, for 30 minutes at 30° C., in a final volume of 30 μl comprising 50 mM Hepes, 19 mM MgCl$_2$, 125 μM ATP, 5 mM NaPPi, 1 mM EDTA, 1 mM DTT, 2 mM Na$_3$VO$_4$ and 25 μM of peptide AMARAA biotinyl (Biot-NH-AMARAASAAALARRR-COOH).
The phosphorylation of the peptide AMARAA is then measured according to a Delfia protocol (Perkin-Elmer), using a europium-labelled anti-phospho-serine specific antibody.
The AMPK used in this test is a partially purified protein from rat liver.

The percentage of activation is calculated relative to the basal activity (100%) obtained in the absence of AMP.

B) Results

| Example No. | % Activation at 200 μM |
|---|---|
| 43 | 229 |
| 44 | 147 |
| 47 | 184 |
| 56 | 289 |
| 58 | 311 |

The invention claimed is:
1. Compound of the formula (1Ca):

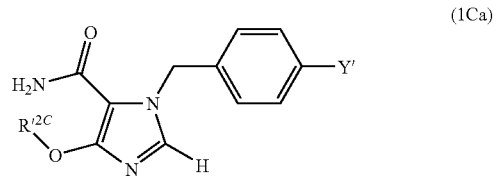

in which:
*R$^{12C}$ represents hydrogen or (C$_1$-C$_8$)alkyl, and
Y' is chosen from

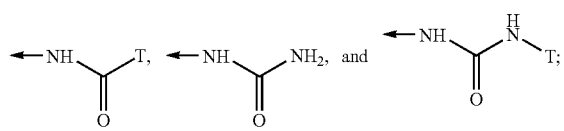

in which T is chosen from:
optionally substituted linear or branched (C$_1$-C$_8$)alkyl;
optionally substituted (C$_3$-C$_{10}$)cycloalkyl;
(C$_6$-C$_{14}$)aryl optionally substituted by one or more groups independently chosen from halogen, cyano, (C$_1$-C$_8$)alkoxy, (C$_3$-C$_8$)cycloalkyl(C$_1$-C$_8$)alkyl, (C$_1$-C$_8$)-alkoxycarbonyl, hydroxycarbonyl and (C$_1$-C$_8$)alkylthio;
(C$_6$-C$_{14}$)aryl(C$_1$-C$_8$)alkyl, the aryl group being optionally substituted by one or more groups independently chosen from halogen, cyano, (C$_1$-C$_8$)alkoxy, (C$_3$-C$_{10}$)cycloalkyl(C$_1$-C$_8$)alkyl, (C$_1$-C$_8$)alkoxycarbonyl, hydroxycarbonyl and (C$_1$-C$_8$)alkylthio;
and the possible geometrical and/or optical isomers, epimers and tautomeric forms thereof,
and also the possible addition salts thereof with a pharmaceutically acceptable acid or base.
2. Compound according to claim 1, of the formula (1Caa):

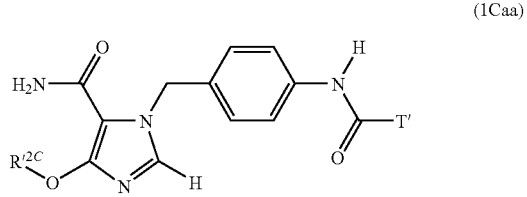

in which R'²ᶜ represents hydrogen, (C₁-C₈)alkyl or (C₂-C₁₄)acyl and T' is as defined for T above, the possible geometrical and/or optical isomers, epimers and tautomeric forms thereof;

and also the possible addition salts thereof with a pharmaceutically acceptable acid or base.

3. Compound according to claim 1, of the formula (1Cb):

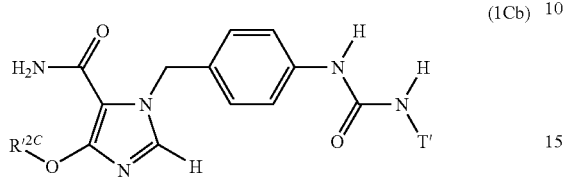

(1Cb)

in which R'²ᶜ represents hydrogen, (C₁-C₈)alkyl or (C₂-C₁₄)acyl and T' is as defined for T above, the possible geometrical and/or optical isomers, epimers and tautomeric forms thereof;

and also the possible addition salts thereof with a pharmaceutically acceptable acid or base.

4. Compound according to claim 1, chosen from:
4-hydroxy-1-[4-(3-methoxybenzoylamino)benzyl]-1H-imidazole-5-carboxamide;
1-(4-acetylaminobenzyl)-4-hydroxy-1H-imidazole-5-carboxamide;
1-(4-benzoylaminobenzyl)-4-hydroxy-1H-imidazole-5-carboxamide;
1-[4-(cyclohexanecarbonylamino)benzyl]-4-hydroxy-1H-imidazole-5-carboxamide;
4-hydroxy-1-[4-(4-methoxybenzoylamino)benzyl]-1H-imidazole-5-carboxamide;
1-[4-(3,3-dimethylbutyrylamino)benzyl]-4-hydroxy-1H-imidazole-5-carboxamide;
4-hydroxy-1-[4-(4-fluorobenzoylamino)benzyl]-1H-imidazole-5-carboxamide;
4-hydroxy-1-{4-[(naphthalene-1-carbonyl)amino]benzyl}-1H-imidazole-5-carboxamide;
1-[4-(3-cyclopentylpropionylamino)benzyl]-4-hydroxy-1H-imidazole-5-carboxamide;
4-hydroxy-1-[4-(3-methoxybenzoylamino)benzyl]-1H-imidazole-5-carboxamide;
1-{4-[2-(4-chlorophenyl)acetylamino]benzyl}-4-hydroxy-1H-imidazole-5-carboxamide;
4-hydroxy-1-[4-(4-chlorobenzoylamino)benzyl]-1H-imidazole-5-carboxamide;
1-(4-hexanoylaminobenzyl)-4-hydroxy-1H-imidazole-5-carboxamide;
4-hydroxy-1-[4-(2-fluorobenzoylamino)benzyl]-1H-imidazole-5-carboxamide;
4-hydroxy-1-[4-(4-methylbenzoylamino)benzyl]-1H-imidazole-5-carboxamide;
4-hydroxy-1-[4-(2-methoxybenzoylamino)benzyl]-1H-imidazole-5-carboxamide;
4-hydroxy-1-{4-[naphthalene-2-carbonyl)amino]benzyl}-1H-imidazole-5-carboxamide;
4-hydroxy-1-{4-[2-(4-nitrophenyl)acetylamino]benzyl}-1H-imidazole-5-carboxamide;
4-hydroxy-1-[4-(2-phenylbutyrylamino)benzyl]-1H-imidazole-5-carboxamide;
1-[4-(2-furan-2-ylacetylamino)benzyl]-4-hydroxy-1H-imidazole-5-carboxamide;
4-methoxy-1-{4-[(naphthalene-1-carbonyl)amino]benzyl}-1H-imidazole-5-carboxamide;
4-acetyloxy-1-[4-(4-acetylamino)benzyl]-1H-imidazole-5-carboxamide;
4-hydroxy-1-[4-(3-phenylureido)benzyl]-1H-imidazole-5-carboxamide;
4-hydroxy-1-{4-[3-(4-methoxyphenyl)ureido]benzyl}-1H-imidazole-5-carboxamide;
4-hydroxy-1-{4-[3-(4-chlorophenyl)ureido]benzyl}-1H-imidazole-5-carboxamide;
1-[4-(3-cyclohexylureido)benzyl]-4-hydroxy-1H-imidazole-5-carboxamide;
1-[4-(3-cyclopentylureido)benzyl]-4-hydroxy-1H-imidazole-5-carboxamide;
4-hydroxy-1-[4-(3-naphthalen-1-ylureido)benzyl]-1H-imidazole-5-carboxamide;
4-hydroxy-1-[4-(3-naphthalen-2-ylureido)benzyl]-1H-imidazole-5-carboxamide;
4-hydroxy-1-{4-[3-(5,6,7,8-tetrahydronaphthalen-1-yl)ureido]benzyl}-1H-imidazole-5-carboxamide;
1-[4-(3-ethylureido)benzyl]-4-hydroxy-1H-imidazole-5-carboxamide;
1-[4-(3-benzylureido)benzyl]-4-hydroxy-1H-imidazole-5-carboxamide;
4-hydroxy-1-[4-(3-m-tolylureido)benzyl]-1H-imidazole-5-carboxamide;
4-hydroxy-1-{4-[3-(3-methoxyphenyl)ureido]benzyl}-1H-imidazole-5-carboxamide;
1-{4-[3-(2-fluorobenzyl)ureido]benzyl}-4-hydroxy-1H-imidazole-5-carboxamide;
4-hydroxy-1-{4-[3-(2-methoxyphenyl)ureido]benzyl}-1H-imidazole-5-carboxamide;
4-hydroxy-1-{4-[3-(4-ethylphenyl)ureido]benzyl}-1H-imidazole-5-carboxamide;
4-hydroxy-1-{4-[3-(3-methylsulfanylphenyl)ureido]benzyl}-1H-imidazole-5-carboxamide;
4-hydroxy-1-{4-[3-(4-methylsulfanylphenyl)ureido]benzyl}-1H-imidazole-5-carboxamide;
4-hydroxy-1-[4-[3-indan-5-ylureido]benzyl]-1H-imidazole-5-carboxamide;
4-hydroxy-1-{4-[3-(4-fluorophenyl)ureido]benzyl}-1H-imidazole-5-carboxamide;
4-hydroxy-1-{4-[3-(2-chlorophenyl)ureido]benzyl}-1H-imidazole-5-carboxamide;
4-hydroxy-1-{4-[3-(2-trifluoromethylphenyl)ureido]benzyl}-1H-imidazole-5-carboxamide;
4-hydroxy-1-{4-[3-(3-trifluoromethylphenyl)ureido]benzyl}-1H-imidazole-5-carboxamide;
4-hydroxy-1-{4-[3-(4-trifluoromethylphenyl)ureido]benzyl}-1H-imidazole-5-carboxamide;
ethyl 3-{3-[4-(5-carbamoyl-4-hydroxyimidazol-1-ylmethyl)phenyl]ureido}benzoate;
3-{3-[4-(5-carbamoyl-4-hydroxyimidazol-1-ylmethyl)phenyl]ureido}benzoic acid;
ethyl 4-{3-[4-(5-carbamoyl-4-hydroxyimidazol-1-ylmethyl)phenyl]ureido}benzoate;
4-{3-[4-(5-carbamoyl-4-hydroxyimidazol-1-ylmethyl)phenyl]ureido}benzoic acid;
ethyl 2-{3-[4-(5-carbamoyl-4-hydroxyimidazol-1-ylmethyl)phenyl]ureido}benzoate; and
ethyl {3-[4-(5-carbamoyl-4-hydroxyimidazol-1-ylmethyl)phenyl]ureido}acetate.

5. Process for the preparation of a compound according to claim 2 according to the following reaction scheme:

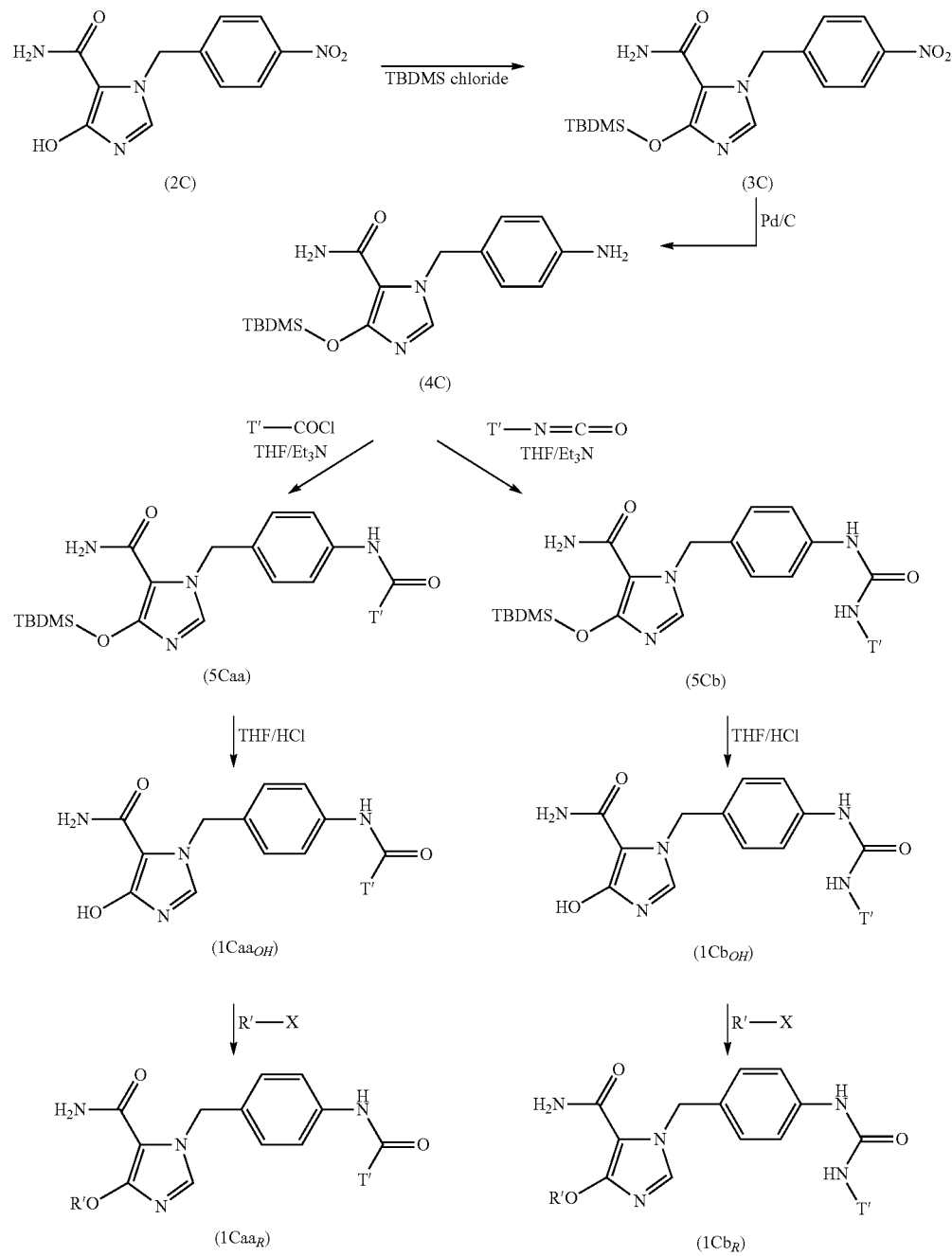

in which scheme R' has the same definition as $R'^{2C}$, with the exception of hydrogen, and $R'^{2C}$ and T' are as defined in claim 2, the set of compounds of the formulae ($1Caa_{OH}$) and ($1Caa_R$), on the one hand, and ($1Cb_{OH}$) and ($1Cb_R$), on the other hand, forming the set of compounds of the formulae (1Caa) and (1Cb), respectively.

6. Pharmaceutical composition comprising a pharmaceutically effective amount of at least one compound of claim 1, in combination with one or more pharmaceutically acceptable vehicles.

7. A method for treating type II diabetes, insulin resistance, insulin resistance syndrome X or obesity, which comprises administering a compound of claim 1.

8. The method for treating non-insulin-dependent diabetes, dyslipidaemia or obesity, which comprises administering a compound of claim 1.

9. The method for treating arterial hypertension, microvascular and macrovascular cardiac complications of diabetes, retinopathy or neuropathy, which comprises administering a compound of claim 1.

10. The method according to claim 7, treating type II diabetes and its effects on the kidneys, the heart, the eyes, the blood vessels and the nerves.

11. Process for the preparation of a pharmaceutical composition which comprises adding one or more solid, liquid or semi-liquid vehicles to at least one compound of claim 1.

12. Process for the preparation of a compound according to claim 3 according to the following reaction scheme:

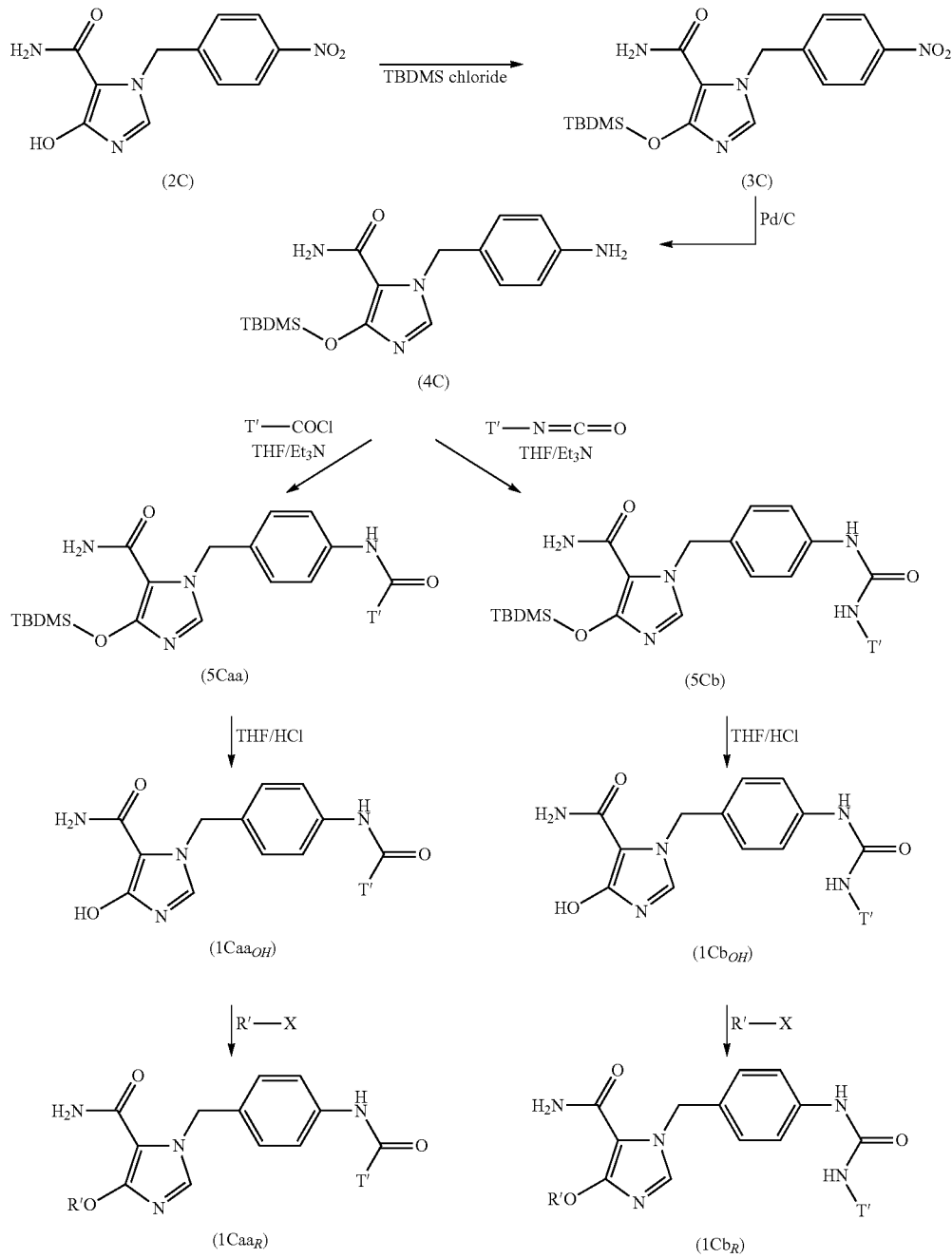

in which scheme R' has the same definition as $R'^{2C}$, with the exception of hydrogen, and $R'^{2C}$ and T' are as defined in claim 3, the set of compounds of the formulae $(1Caa_{OH})$ and $(1Caa_R)$, on the one hand, and $(1Cb_{OH})$ and $(1Cb_R)$, on the other hand, forming the set of compounds of the formulae (1Caa) and (1Cb), respectively.

13. A method for treating type II diabetes, insulin resistance, insulin resistance syndrome X or obesity, which comprises administering a compound of claim 2.

14. A method for treating type II diabetes, insulin resistance, insulin resistance syndrome X or obesity, which comprises administering a compound of claim 3.

15. A method for treating type II diabetes, insulin resistance, insulin resistance syndrome X or obesity, which comprises administering a compound of claim 4.

* * * * *